(12) United States Patent
Wells et al.

(10) Patent No.: US 10,040,844 B2
(45) Date of Patent: Aug. 7, 2018

(54) PROTEOLYTIC RELEASE OF CELL SURFACE ANTIGENS FOR PHAGE BIOPANNING

(71) Applicant: The Regents of the University of California, Oakland, CA (US)

(72) Inventors: James A. Wells, Burlingame, CA (US); Juan Diaz, Colma, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 73 days.

(21) Appl. No.: 14/920,816

(22) Filed: Oct. 22, 2015

(65) Prior Publication Data
US 2016/0115220 A1 Apr. 28, 2016

Related U.S. Application Data

(60) Provisional application No. 62/067,292, filed on Oct. 22, 2014.

(51) Int. Cl.
| | | |
|---|---|---|
| *C40B 30/04* | (2006.01) | |
| *C07K 16/00* | (2006.01) | |
| *G01N 33/68* | (2006.01) | |
| *C07K 16/28* | (2006.01) | |

(52) U.S. Cl.
CPC ....... *C07K 16/005* (2013.01); *G01N 33/6845* (2013.01); *G01N 33/6854* (2013.01); *C07K 16/28* (2013.01); *C07K 16/2878* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 5,821,337 | A | 10/1998 | Carter et al. |

(Continued)

FOREIGN PATENT DOCUMENTS

| | | |
|---|---|---|
| WO | WO 1992/011018 | 7/1992 |
| WO | WO 1994/013804 | 6/1994 |
| WO | WO 2003/011161 | 2/2003 |

OTHER PUBLICATIONS

Matthews et al. (May 21, 1993) Science vol. 260 pp. 1113 to 1117.*

(Continued)

*Primary Examiner* — Christian C Boesen
(74) *Attorney, Agent, or Firm* — Morgan, Lewis & Bockius LLP; Jeffry S. Mann; Louis T. Nguyen

(57) ABSTRACT

The invention described herein features methods of isolating monoclonal antibodies or polypeptides that bind to a cell surface expressed antigen. The method of catch and release utilizes engineered protease site for cleavage antigen-antibody or antigen-polypeptide complexes. In some embodiments the protease cleavage site to cleave the complexes is an exogenous protease to mammalian cell. In various embodiments the protease cleavage site to cleave the complexes is an endogenous protease to mammalian cell.

9 Claims, 11 Drawing Sheets

(56) References Cited

U.S. PATENT DOCUMENTS

| | | |
|---|---|---|
| 5,859,205 A | 1/1999 | Adair et al. |
| 6,054,297 A | 4/2000 | Carter et al. |
| 6,180,370 B1 | 1/2001 | Queen et al. |
| 6,407,213 B1 | 6/2002 | Carter et al. |

OTHER PUBLICATIONS

Yang et al (May 9, 2013) Cell vol. 153 pp. 896 to 909.*
Baca et al., 1997, J. Biol. Chem. 272(16):10678-10684.
Bird et al., 1988, Science 242:423-426.
Carter et al., 1992, Proc Natl Acad Sci USA 89:4285-9.
Gorman et al., 1991, Proc. Natl. Acad. Sci. USA 88:4181-4185.
He et al., 1998, J. Immunol. 160: 1029-1035.
Holliger et al., 1993, Proc. Natl. Acad. Sci. U.S.A. 90:6444-6448.
Hu et al., 1996, Cancer Res. 56:3055-3061.
Huston et al., 1988, Proc. Natl. Acad. Sci. U.S.A. 85:5879-5883.
Jones, 1986, Nature 321:522-525.
Krauss et al., 2003, Protein Engineering 16(10):753-759.
McCafferty, J. et al., 1990, Nature, vol. 348, pp. 552-554.
O'Connor et al., 1998, Protein Eng 11:321-8.
Presta et al., 1997, Cancer Res. 57(20):4593-9.
Queen et al., 1989, Proc Natl Acad Sci, USA 86:10029-33.
Rader et al., 1998, Proc. Natl. Acad. Sci. USA 95: 8910-8915.
Riechmann et al., 1988; Nature 332:323-329.
Roguska et al., 1994, Proc. Natl. Acad. Sci. USA 91:969-973.
Rosok et al., 1996, J. Biol. Chem. 271(37): 22611-22618.
Roque et al., 2004, Biotechnol. Prog. 20:639-654.
Tomlinson et. al., 2000, Methods Enzymol. 326:461-479.
Verhoeyen et al., 1988, Science 239:1534-1536.
Ward et al., 1989, Nature 341:544-546.
Wu et al., 1999, J. Mol. Biol. 294:151-162.

* cited by examiner

Figure 5
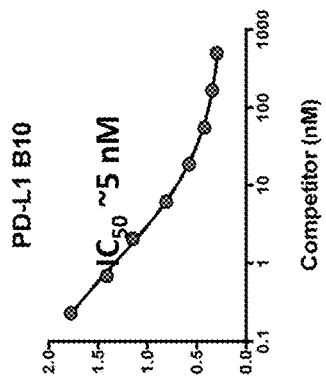
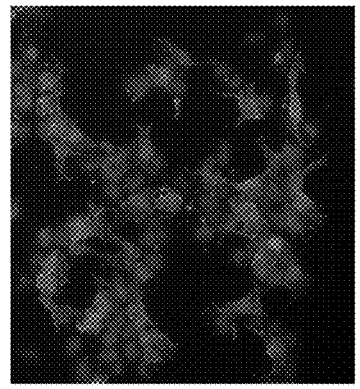
A PD-L1
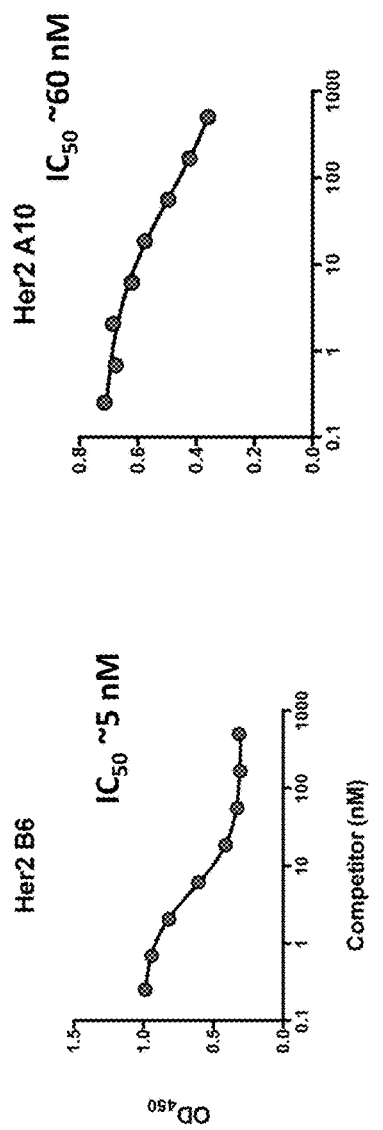
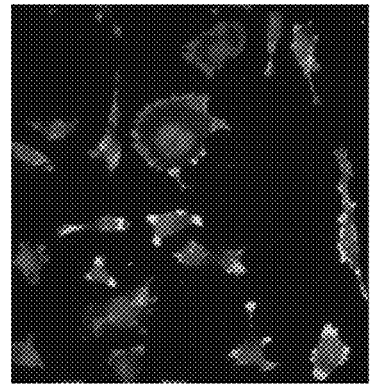
B Her2

Figure 6
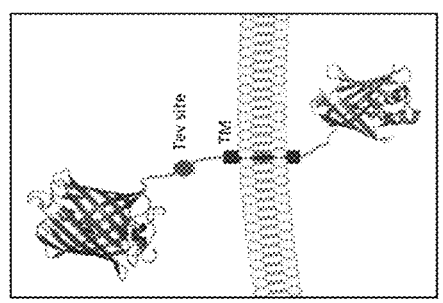
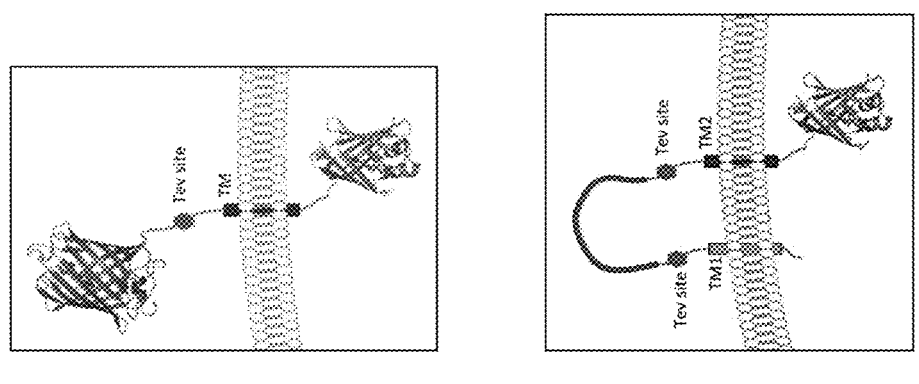
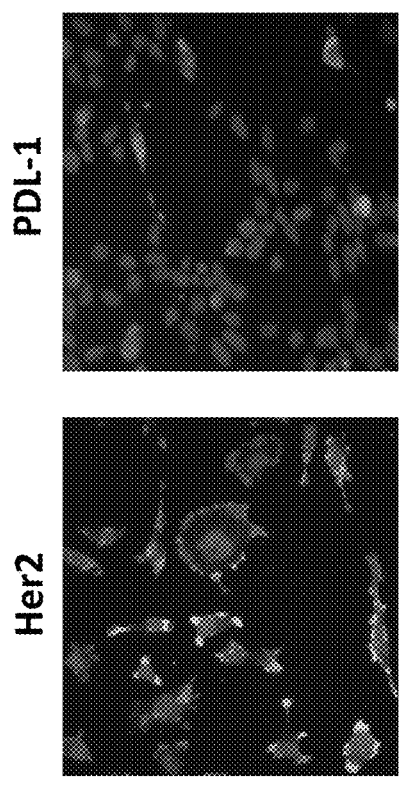
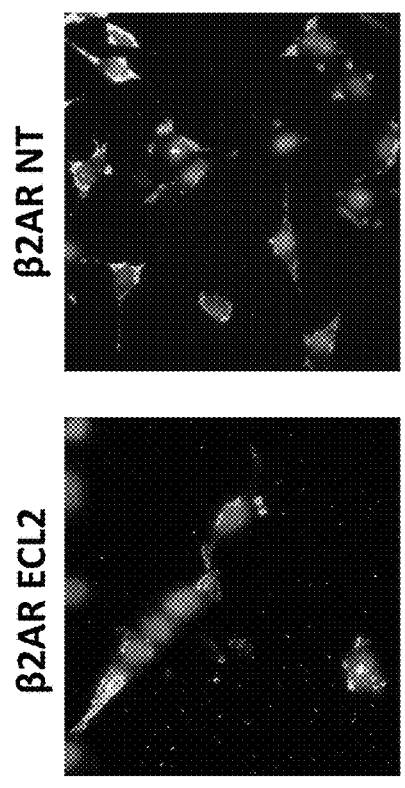

PROTEOLYTIC RELEASE OF CELL SURFACE ANTIGENS FOR PHAGE BIOPANNING

CROSS REFERENCE TO RELATED APPLICATIONS

The present application claims benefit of U.S. Provisional Application No. 62/067,292 filed on Oct. 22, 2014, which is incorporated herein by reference in its entirety.

FIELD OF THE INVENTION

The present invention provides in one embodiment a method of selecting monoclonal antibodies that bind to a cell surface expressed antigen using a catch and release biopanning technique.

BACKGROUND

In the development of biosensors for the early detection of disease, the availability of high specificity and affinity ligands for biomarkers that are indicative of a pathogenic process is important. Biopanning of phage displayed peptide libraries on intact cells has proven to be a successful route for the identification of cell-specific ligands. The peptides selected from these combinatorial libraries are often able to distinguish between diseased cells and their normal counterparts as well as cells in different activation states. These ligands are small and chemical methodologies are available for their regiospecific derivatization. As such, they can be incorporated into a variety of different diagnostic and therapeutic platforms. However, current methods for generating monoclonal antibodies against cell surface expressed antigens are inefficient and time-consuming, requiring the overproduction and/or purification of each extracellular target of interest. Cell surface proteins are dynamically regulated and their expression profiles can change depending on cellular stress or disease states.

Although there has been considerable effort spent on optimizing in vitro phage and yeast display techniques, selection methods using large antibody libraries or polypeptide libraries against these membrane-bound targets on whole cells pose significant problems. Major limitations remain in the existing art, such as distinguishing specific and non specific antibody-antigen complexes, wherein the antigen is the cell surface protein of interest (POI), isolation from the mixture of antibodies, directing antibodies towards the protein of interest or to the cell surface or family of proteins of interest (FPOI), and binding of antibodies to the background protein on the cell surface.

The general approach to remove antibodies or polypeptides bound to background protein comprises steps of depleting phage-antibody or phage-polypeptide libraries that are bound to background proteins and then adding those surviving phage to cells containing the POI. This approach is cumbersome and requires multiple selections. Another major limitation of generating and isolating antibodies or polypeptides to a specific protein of interest is the over-expression of the protein of interest; it is known that over-expression can upregulate other proteins not related to the POI and increase background antibodies, thereby complicating antibody-POI complex selection and increasing the non-specific binding. Thus, alternate methods for selection of antibodies that bind to protein of interests are needed.

SUMMARY

Provided herein are methods of selecting monoclonal antibodies that bind to a cell surface expressed antigen. This process can be summarized as catch and release biopanning.

In one aspect, provided herein is a method of selecting an antibody that binds to a protein of interest. In certain embodiments, the method includes the steps of: a) providing a composition that includes a mammalian cell expressing a protein of interest on the cell surface, wherein the protein of interest includes at least one unique protease cleavage site; b) exposing the mammalian cell to a library of phage-antibody constructs; c) binding one or more phage-antibody constructs from the library to the protein of interest to form one or more antigen-antibody complexes, wherein the antigen is the protein of interest; d) releasing the one or more antigen-antibody complexes from the cell by cleaving the protease cleavage site with a protease; and e) propagating the phage of the released antigen-antibody complexes and identifying the antibody that binds to the protein of interest; thereby selecting the antibody.

In one embodiment, steps (b) through (e) are repeated. In another embodiment, steps (b) through (e) are repeated from about 2 to about 10 times. In another embodiment, unbound phage is removed prior to the repeating of steps (b) through (e). In another embodiment, the protease is a Tobacco Etch Virus nuclear inclusion endopeptidase (TEV protease). In another embodiment, the protease cleavage site is heterologous to the protein of interest. In another embodiment, the protease cleavage site is endogenous to the protein of interest. In another embodiment, the protease is heterologous to the mammalian cell. In another embodiment, the protease is endogenous to the mammalian cell. In another embodiment, the protease is exogenous to the mammalian cell. In another embodiment, the method further comprises the step of using the selected antibody to isolate the protein of interest. In another embodiment, the protein of interest comprises a transmembrane domain. In another embodiment, the protein of interest comprises at least two transmembrane domains. In another embodiment, the protein of interest comprises at least two protease cleavage sites.

BRIEF DESCRIPTION OF THE DRAWINGS

FIG. 5 are graphs showing that antibodies selected for binding to PDL-1 (A) and Her2 (B) antigen using the subject methods exhibit high affinity antigen binding.

FIG. 6 illustrates two embodiments of the subject protein of interests described herein. Proteins of interest can be displayed in a "single pass" format (Her2, PDL-1, A and B) or a "multi-pass" format (β2AR ECL2 and β2AR NT, C and D).

As shown in FIG. 6, the protein of interest included a FLAG tag and GFP for detection and a TEV protease cleavage site.

DETAILED DESCRIPTION

Introduction

Figure 1:
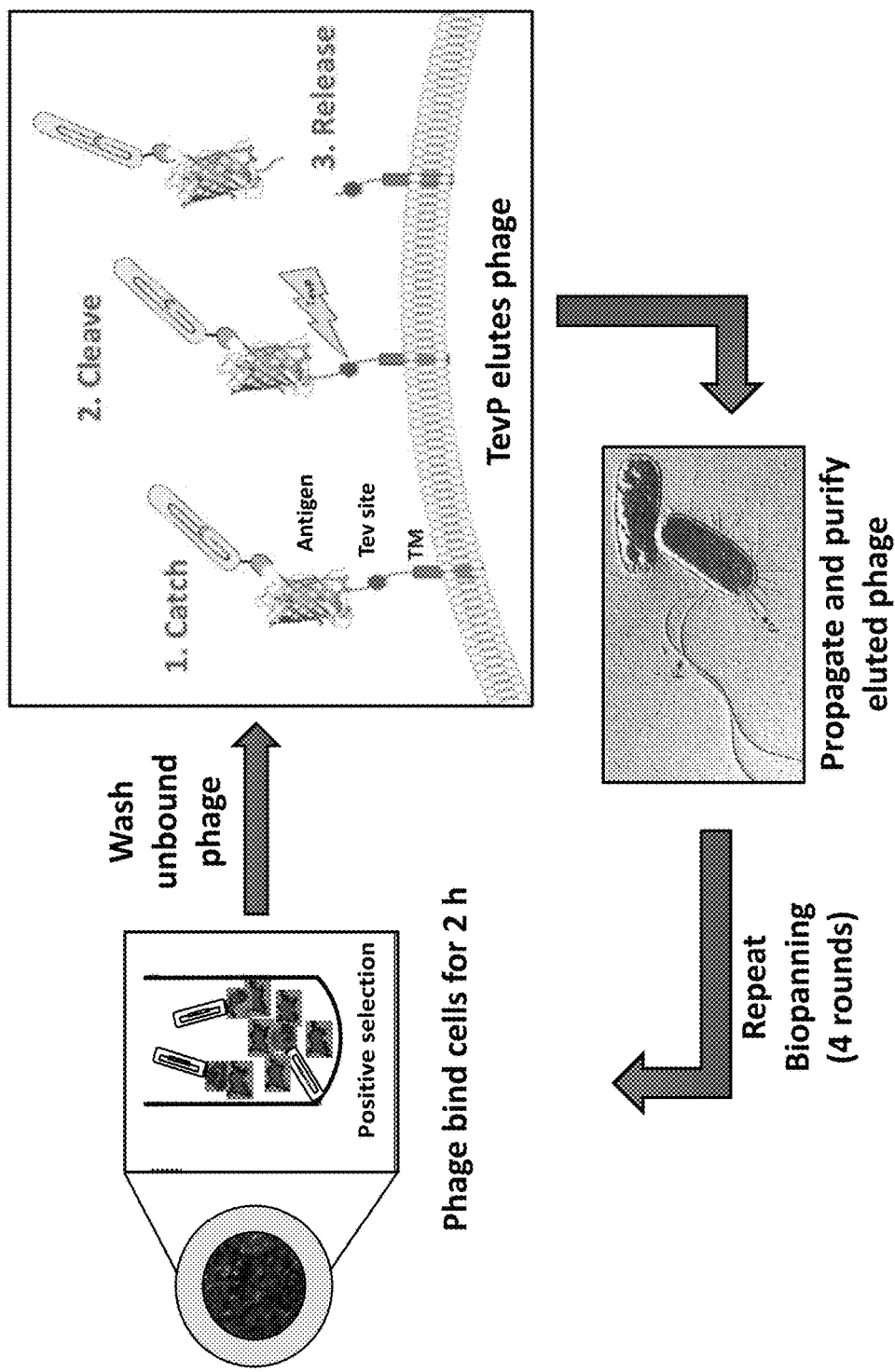
FIG. 1 is an exemplary schematic of a catch and release biopanning process.

Provided herein are methods for selecting high affinity antibodies or polypeptides against a cell surface antigen.

The technology described provides methods and compositions for the rapid capture and selective proteolytic release of antibody or polypeptide fragments bound to extracellularly displayed targets. The advantage of this approach is the highly specific means of removing from cells (by proteolysis) the specific antigen-phage antibody complex or antigen-phage polypeptide complex of interest from cells. This catch and release biopanning takes advantage of a protease cleavage site engineered in the protein of interest (POI); after formation of POI-phage complexes by incubation the phages with cells possessing the POI, the unbound phages are removed from the incubation composition; the addition of protease corresponding to the protease cleavage site releases antigen-phage complexes. Phages are propagated and the biopanning process may be repeated several times.

The mammalian cell surface antigen described herein is expressed as a cell surface molecule or a cell surface receptor and can, for example, be an oncology target.

The protease that recognizes the cleavage site of the POI can be exogenous to a mammalian cell or endogenous to a mammalian cell, such as naturally occurring "sheddases"; yet the substrates that sheddases cleave are often unknown or incompletely known. The protease cleavage site in the POI may also be naturally occurring or heterologous (e.g., engineered) to the protein.

The process provided herein is a robust and rapid way of selecting functional antibodies or polypeptides against therapeutically relevant disease targets. The subject methods and compositions provided may be used as a platform for the identification of unknown extracellular protease substrates such as "sheddases" and also for the generation of selective monoclonal antibody against "sheddases".

Definitions

Unless specifically indicated otherwise, all technical and scientific terms used herein have the same meaning as commonly understood by those of ordinary skill in the art to which this invention belongs. In addition, method or materials that are substantially equivalent to a method or material described herein can be used in the practice of the present invention. For purposes of the present invention, the following terms are defined.

The term "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized. Antibodies exist, e.g., as intact immunoglobulins or as a number of well-characterized fragments produced by digestion with various peptidases (see Fundamental Immunology (Paul ed., 3rd Ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., 1990, Nature 348:552-554).

In some embodiments, the antibodies are full length. Herein "full length antibody" means the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426; Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

In some embodiments, the antibody can be a mixture from different species, e.g., a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to nonhuman antibodies that have had the variable-domain framework regions swapped for sequences found in human antibodies. The creation of such antibodies is described in, e.g., WO 92/11018; Jones, 1986, Nature 321:522-525; Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9; Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference.

In some embodiments the antibodies are diabodies. In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

The term "antigen" refers to a molecule capable of being bound by an antibody. An antigen is additionally capable of inducing a humoral immune response and/or cellular immune response leading to the production of B and/or T-lymphocytes.

The term "polypeptide" or "protein" refers to a polymer of two or more amino acid residues. The terms apply to amino acid polymers in which one or more amino acid residue is an artificial, chemical analogue of a corresponding naturally occurring amino acid, as well as to polymers of naturally occurring amino acids. The term "recombinant protein" refers to a protein that is produced by expression of a nucleotide sequence encoding the amino acid sequence of the protein from a recombinant DNA molecule.

The term "protein of interest" as used herein refers to a peptide comprising an amino acid sequence recognized by the engineered antibodies described herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such unnatural amino acid analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "protease" (also termed peptidase or proteinase) as used herein refers to any enzyme that performs proteolysis, that is, begins protein catabolism by hydrolysis of the peptide bonds that link amino acids together in the polypeptide chain forming the protein. Proteases have evolved multiple times, and different classes of protease can perform the same reaction by completely different catalytic mechanisms. Proteases can be found in animals, plants, bacteria, and viruses.

The term "protease cleavage site" (also termed peptidase cleavage site or proteinase cleavage site) in a protein as used herein refers sequence known as proteolytic signatures, where the protein is recognized by a proteolytic enzyme and cleaved at a specific site in the protein.

In some embodiments the term "heterologous protease cleavage site" refers to a sequence of amino acids cleaved by proteases, which does not exist naturally in the protein but is instead engineered.

The term "endogenous protease cleavage site" describes a sequence of amino acids cleaved by mammalian cell protease, where the sequence is native to the protein, e.g., naturally occurring.

The term endogenous can also refer to a protease that is native to and expressed by the cell. An exogenous protease is one that is not expressed by the cell and is added to the cell culture.

The term "biopanning" described herein is an affinity selection technique which selects for peptides that bind to a given target. All peptide sequences obtained from biopanning using combinatorial peptide libraries have been stored in a special database with the name MimoDB, which is freely available. This technique is often used for the selection of antibodies too.

Biopanning involves several steps for peptide selection. The first step is to have phage display libraries prepared. This involves inserting foreign desired gene segments (e.g., that encode antibodies) into a region of the bacteriophage genome, so that the peptide product will be displayed on the surface of the bacteriophage viron. The most often used are genes pIII or pVIII of bacteriophage M13. The next step is the capturing step. It involves conjugating the phage library to the desired target. This procedure is termed panning. It utilizes the binding interactions so that only specific peptides presented by bacteriophage are bound to the target. For example, selecting antibody presented by bacteriophage with coated antigen in microtiter plates.

The washing step comes after the capturing step to wash away the unbound phages from solid surface. Only the bound phages with strong affinity are kept. The final step involves the elution step where the bound phages are eluted through changing of pH or other environment conditions.

The resulting filamentous phages can infect Gram negative bacteria once again to produce phage libraries. The cycle can occur many times resulting with strong affinity binding peptides to the target.

The term "sheddase" refers to a membrane-bound enzyme that cleaves extracellular portions of transmembrane proteins, releasing the soluble domains from the cell surface.

The term "CDR" as used herein specifies the Complementarity Determining Region (see, for example, Harlow and Lane, "Antibodies, a Laboratory Manual," CSH Press, Cold Spring Harbour, 1988). A CDR is a relatively short amino acid sequence found in the variable (V) domains of an antibody. Each variable domain (the heavy chain VH and light chain VL) of an antibody comprises three complementarity determining regions sometimes called hypervariable regions, flanked by four relatively conserved framework regions or "FRs." The six CDRs of an antibody essentially determine the specificity of an antibody and make the contact with a specific ligand.

In one aspect provided herein is a method of selecting an antibody that binds to a protein of interest (FIG. 1). A composition is first provided that includes a mammalian cell expressing a protein of interest on the cell surface, wherein the protein of interest includes at least one unique protease cleavage site. The mammalian cell is then exposed to a library of phage-antibody constructs. Upon exposure to the library of phage antibody constructs, one or more phage-antibody constructs from the library is bound to the protein of interest to form one or more antigen-antibody complexes, wherein the antigen is the protein of interest. Following binding, the mammalian cells are optionally washed to remove any unbound phage-antibodies. The one or more antigen-antibody complexes are then released from the cell by cleaving the protease cleavage site with a protease. Phages from the antigen-antibody complexes are then propagated and antibodies that bind to the protein of interest are identified using any suitable technique (e.g., sequence techniques), thereby selecting the antibody. Aspects of the subject method are discussed in detail below.

I. PROTEINS OF INTEREST

In some embodiments, the subject methods provided herein are for the selection of antibodies or binding proteins that bind to a protein of interest (POI) expressed on the surface of a cell. The subject methods and compositions can be used to select for antibody or binding proteins that bind any POI. The POI can be a protein that is naturally expressed on a cell surface (e.g., a cell surface receptor) or a protein that is not naturally expressed on a cell surface (e.g., an intracellular protein). In some embodiments, the POI is cell surface protein. In certain embodiments, the POI is an intracellular protein. POIs that are not naturally expressed on a cell surface can be expressed on cellular surfaces by fusion to a cell transmembrane domain (TM domain). Any Suitable TM domains can be used for cell surface expression of POIs that are not naturally expressed on cellular surfaces. In some embodiments the POI is fused to the transmembrane domain of a cell surface antigen, a cellular receptor, an adhesion molecule or a transport domain. In certain embodiments, the transmembrane domain is the transmembrane domain of CD1, CD2, CD4, CD8, CD28, I-CAM, N-CAM, lymphocyte function associated antigen-3 (LFA-3), neurocytoplasmic protein (NCP-3), poly-Ig receptor, myelin-associated glycoprotein (MAG), high affinity IgE receptor, the major glycoprotein of peripheral myelin (Po), platelet derived growth factor receptor, colony stimulating factor-1 receptor, macrophage an Fc receptor, or an Fc gamma receptor.

The transmembrane domains can allow for the expression of the POI in a "single" format, using a single transmembrane domain or in a "multi-pass" format, using more than one transmembrane domain (FIG. 6). In some embodiments, the POI is flanked by a transmembrane domain at its N- and C-terminus. In such embodiments, the transmembrane domain flanking the N- and C-terminus of the POI can be the same transmembrane domain or different transmembrane domains.

In certain embodiments, the POI is a cell surface receptor. Cell surface receptors (membrane receptors, transmembrane receptors) are specialized integral membrane proteins that take part in communication between the cell and the outside world. Extracellular signaling molecules (usually hormones, neurotransmitters, cytokines, growth factors or cell recognition molecules) bind to the receptor, triggering changes in the function of the cell in a process termed signal transduction. The binding initiates a chemical change on the intracellular side of the membrane. In this way, the receptors play a unique and important role in cellular communications and signal transduction.

Based on structural and functional similarities, membrane receptors are mainly divided into 3 classes:
1. The ion channel-linked receptor
2. The enzyme-linked receptor
3. G protein-coupled receptors are integral membrane proteins that possess seven membrane-spanning domains or transmembrane helices.

In some embodiments, the POI is a oncology target. The use of monoclonal antibodies for the therapy of cancer is one of the major contributions of tumor immunology to cancer patients. This success is built on decades of scientific research aimed at serological characterization of cancer cells, techniques for generating optimized antibodies to tumor targets, detailed investigation of signaling pathways relevant to cancer cells, and an understanding of the complex interplay between cancer cells and the immune system. The clinical development of antibodies is inextricably linked to disciplined and detailed exploration of the properties of antibodies in vivo and assessment of functional effects on cancer cells. Exemplary oncology targets for antibody selection using the target methods include, but are not limited to, CD20, CD30, CD33, CD52, CD55, CD59, CD147, CDCP1, NT5E, EpCAM, CEA, gpA33, Mucins, TAG-72, Carbonic anhydrase IX, PSMA, Folate binding protein, Gangliosides (e.g., CD2, CD3, GM2), Lewis-$\gamma^2$, VEGF, VEGFR 1/2/3, $\alpha V\beta 3$, $\alpha 5\beta 1$, ErbB1/EGFR, ErbB1/HER2, ErB3, c-MET, IGF1R, EphA3, TRAIL-R1, TRAIL-R2, RANKL, FAP, Tenascin, PDL-1, BAFF, HDAC, ABL, FLT3, KIT, MET, RET, IL-1β, ALK, RANKL, mTOR, CTLA-4, IL-6, IL-6R, JAK3, BRAF, PTCH, Smoothened, PlGF, ANPEP, TIMP1, PLAUR, PTPRJ, LTBR, and ANTXR1.

Figure 11:
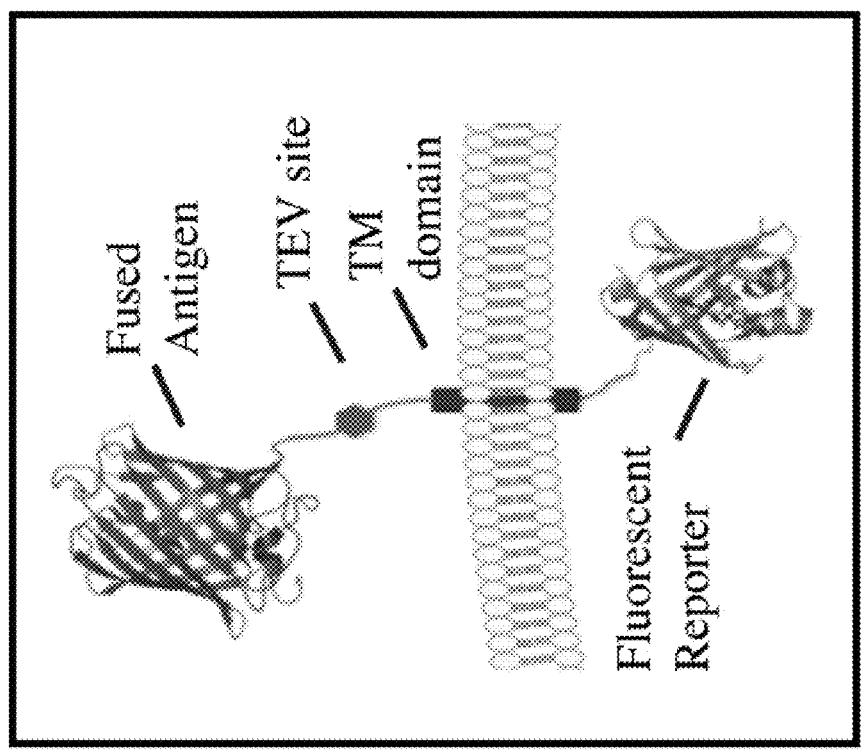
FIG. 11 shows an embodiment of a POI construct that can be used with the subject method wherein a reporter protein is expressed intracellularly.

In certain embodiments, the POI includes one or more reporters and/or tags that allows for the detection of expression and/or isolation of the POI. Reporters include, but are not limited to alkaline phosphatase, galactosidase, peroxidase, luciferase and green fluorescent protein. Tags include, but are not limited to, chitin binding protein (CBP), maltose binding protein (MBP), glutathione-S-transferase (GST), poly(His), FLAG tag, V5-tag, Myc-tag and HA-tag. Such reporters and tags can be extracellular or intracellular (FIG. 11). In some embodiments, the POI includes 2, 3, 4, 5, 6, 7, 8, 9, 10, 11, 12, 13, 14, or 15 different tags or reporters or combinations thereof. In some embodiments, the POI includes a fluorescent reporter. In certain embodiments, the fluorescent reporter is expressed extracellularly. In some embodiments, the fluorescent reporter is expressed intracellularly. In some embodiments, the POI includes a FLAG tag. In exemplary embodiments, the POI includes a fluorescent reporter and a FLAG tag (See, e.g., FIG. 7).

II. ENGINEERING/EXPRESSION OF PROTEINS OF INTEREST

A. Protease Cleavage Sites

1. Exogenous Protease Cleavage Sites

In some embodiments, the POI includes at least one protease cleavage site. In certain embodiments, the protease cleavage site is located extracellularly in such a manner that allows for the cleavage of the POI from a cell surface. Upon binding of phage expressing an antibody or binding protein that binds the POI to form an antigen-antibody complex, the antigen-antibody complex is released from the cell expressing the POI by contacting the one or more cleavage sites of the POI with a protease that cleaves the cleaveage site. In certain embodiments, the number of cleavage sites included with the POI will allow for the complete cleavage of the extracellular portion of the POI from the cell expressing the POI. In some embodiments, the POI is expressed in a single format, wherein only one protease cleavage site is included with the POI (FIG. 6B). In some embodiments, the POI is expressed in a multi-pass format, wherein two or more protease cleavage sites are included with the POI (FIG. 6D). In some embodiments, the POI is flanked by a protease cleavage sequence at each of its N- and C-terminus.

Proteases occur in all organisms, from prokaryotes to eukaryotes to viruses. These enzymes are involved in a multitude of physiological reactions from simple digestion of food proteins to highly regulated cascades. In some embodiments, the exogenous protease cleavage site is a non-mammalian protease. In various embodiments, the protease is a plant, bacterial or viral protease.

Proteolysis can be highly promiscuous such that a wide range of protein substrates are hydrolyzed. Conversely, some proteases are highly specific and only cleave substrates with a certain amino acid sequence. Blood clotting (such as thrombin) and viral polyprotein processing (such as TEV protease) requires this level of specificity in order to achieve precise cleavage events.

Any suitable protease cleavage site can be use with the subject methods provided herein. In certain embodiments, the protease cleavage site is an exogenous protease cleavage site. In some embodiments, the protease cleavage site is a heterologous protease cleavage site. Exemplary protease cleavage sites that can be used with the subject methods include, but are not limited to, enteropeptidase cleavage sites (DDDDK\); (SEQ ID NO:10) thrombin cleavage sites (LVPR\GS) (SEQ ID NO:11); Factor Xa cleavage sites (LVPR\GS) (SEQ ID NO:11); TEV Protease cleavage sites (ENLYFQ\G (SEQ ID NO:12) or ENLYFQ\S(SEQ ID NO: 13)); and Rhinovirus 3C Protease cleavage sites (LEVLFQ\GP)(SEQ ID NO:14), where '\' denotes the cleaved peptide bond.

In some embodiments, the POI of the present invention includes a TEV protease cleavage site. TEV protease (also called Tobacco Etch Virus nuclear inclusion endopeptidase) is a highly sequence-specific cysteine protease from Tobacco Etch Virus (TEV). It is a member of the PA clan of chymotrypsin-like proteases. TEV proteases can be used for the controlled cleavage of fusion proteins in vitro and in vivo. For example, for TEV protease, the preferred native cleavage sequence was first identified by examining the cut sites in the native polyprotein substrate for recurring sequence. The consensus for these native cut sites is ENLYFQ\S(SEQ ID NO: 13) and ENLYFQ\G (SEQ ID NO:12) where '\' denotes the cleaved peptide bond. Residues of the substrate are labeled P6 to P1 before the cut site and P1 after the cut site. Early works also measured cleavage of an array of similar substrates to characterize how specific the protease was for the native sequence.

Studies have subsequently used sequencing of cleaved substrates from a pool of randomized sequences to determine preference patterns. Although ENLYFQ\S(SEQ ID NO:13) is the optimal sequence, the protease is active to a greater or lesser extent on a range of substrates (i.e., it shows some substrate promiscuity). The highest cleavage is of sequences closest to the consensus EXLYΦQ\φ (SEQ ID NO: 15) where X is any residue, Φ is any large or medium hydrophobe and φ is any small hydrophobe.

2. Endogenous Protease Cleavage Sites

In certain embodiments, the protease cleavage site is an endogenous protease cleavage site. The identification of natural substrates and their cleavage sites is pivotal to defining proteolytic pathways; the PROSPER (protease specificity prediction server) database has mapped substrates deposited in MEROPS onto the structural database PDB and obtained a subset of protein substrates with experimentally solved 3D structures. The subset of these substrate PDB structures for the major proteases families are listed, such as Pepsin A, Cathepsin, Caspases, Matrix metallopeptidases, Chymoytrypsin, Membrane-type matrix metallopeptidase etc., and these are currently classified with their catalytic residue into six broad groups.

1. Serine proteases—using a serine alcohol
2. Threonine proteases—using a threonine secondary alcohol
3. Cysteine proteases—using a cysteine thiol
4. Aspartate proteases—using an aspartate carboxylic acid
5. Glutamic acid proteases—using a glutamate carboxylic acid
6. Metalloproteases—using a metal, usually zinc In some embodiments, the protease cleavage site is a sheddase site. Sheddases are membrane-bound enzymes that cleave extracellular portions of transmembrane proteins, releasing the soluble domains from the cell surface. Many sheddases are members of the ADAM or aspartic protease (BACE) protein families. These enzymes can activate a transmembrane protein if it is a receptor (e.g., HER2), or cleave the part of the transmembrane protein which has already bound an agonist (e.g., in the case of EGFR), allowing this agonist to stimulate a receptor on another cell. Hence, sheddases demultiply the yield of agonists. Sheddase inhibitors that act on ADAM10 and ADAM17 sheddases can potentiate anti-cancer therapy.

Members of the ADAM (A Disintegrin And Metalloproteinase) family are cell surface proteins with unique structures, possessing both potential adhesion and protease domains. Sheddase, a generic name for the ADAM metallopeptidase, functions primarily to cleave membrane proteins at the cellular surface. Once cleaved, the sheddases release soluble domains with an altered location and function.

Although a single sheddase may "shed" a variety of substances, multiple sheddases can cleave the same substrate resulting in different consequences. This gene encodes an ADAM family member that cleaves many proteins including TNF-alpha and E-cadherin.

ADAM10 is a sheddase, and has a broad specificity for peptide hydrolysis reactions. In neurons, ADAM10 is the most important enzyme with α-secretase activity for proteolytic processing of the amyloid precursor protein. The proposed active site of ADAM10 has been identified by sequence analysis, and is identical to enzymes in the Snake Venom metalloprotein domain family.

The consensus sequence for catalytically active ADAM proteins is HEXGHNLGXXHD (SEQ ID NO:16). Structural analysis of ADAM17, which has the same active site sequence as ADAM10, suggests that the three histidines in this sequence bind a Zn2+ atom, and that the glutamate is the catalytic residue.

ADAM family members include, but are not limited to, ADAM 2, ADAM 7, ADAM 8, ADAM 9, ADAM 10, ADAM 11, ADAM 12, ADAM 15, ADAM 17, ADAM 18, ADAM 19, ADAM 20, ADAM 21, ADAM 22, ADAM 23, ADAM 28, ADAM 29, ADAM 30, ADAM 33.

In some embodiments, the protease cleavage site is a ADAMTS (A Disintegrin And Metalloproteinase with Thrombospondin Motifs) cleavage site. ADAMTS is a family of peptidases 19 members of this family have been identified in humans. Such peptides have been shown to have roles in connective tissue organization, coagulation, inflammation, arthritis, angiogenesis and cell migration.

Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains.

ADAMTS family members include, but are not limited to, ADAMTS 1, ADAMTS 2, ADAMTS 3, ADAMTS 4, ADAMTS 5, ADAMTS 6, ADAMTS 7, ADAMTS 8, ADAMTS 9, ADAMTS 9, ADAMTS 10, ADAMTS 11, ADAMTS 12, ADAMTS 13, ADAMTS 14, ADAMTS 14, ADAMTS 15, ADAMTS 16, ADAMTS 17, ADAMTS 18, ADAMTS 19, ADAMTS 20. The catalytic site consensus HEXXH (SEQ ID NO:17) is present in all ADAMTS proteins, and all the proteins are presumably catalytically active.

In some embodiments, other sheddases such as L-selectin sheddase (distinguishable from known matrix metalloproteinases in that their activities does not appear to be affected for the natural inhibitors of metalloproteinases (TIMP)) are used as protease cleavage site for the POI.

B. Methods of Engineering/Affecting Expression of any of the Above

In various embodiments, the subject methods provide, in part, polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all modified protein of interest disclosed in the present specification can be encoded by a polynucleotide molecule. It is also envisioned that any and all polynucleotide molecules that can encode a modified POI disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

In some embodiments, well-established molecular biology techniques that may be necessary to make a polynucleotide molecule encoding a modified protein of interest disclosed in the present specification include, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques that are routine procedures well within the scope of one skilled in the art and from the teaching herein. Non-limiting examples of specific protocols necessary to make a poly-nucleotide molecule encoding a modified Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a modified POI are widely available. These protocols are routine procedures well within the scope of one skilled in the art and from the teaching herein.

In some embodiments, a polynucleotide molecule encodes a modified POI as disclosed herein. In some embodiments, a polynucleotide molecule encodes a POI comprising an integrated protease cleavage. In various embodiments, a polynucleotide molecule encodes a modified POI comprising an integrated exogenous protease cleavage site. In various embodiments, a polynucleotide molecule encodes a POI comprising an integrated endogenous protease cleavage site. In some embodiments, a polynucleotide molecule encodes POI with a sheddases cleavage site.

The present invention provides a method of producing a POI disclosed in the present specification, such method comprising the steps of introducing an expression construct comprising a polynucleotide molecule encoding the POI in the present specification into a cell and expressing the expression construct in the cell.

C. Methods of Expression

The methods disclosed in the present specification include, in part, expressing a modified Protein of interest (POI) from a polynucleotide molecule. It is envisioned that any of a variety of expression systems may be useful for expressing a modified POI from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems.

Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin; TX; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001). These protocols are routine procedures well within the scope of one skilled in the art and from the teaching herein.

A variety of cell-based expression procedures are useful for expressing a modified POI encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the VIRAPOWER™ Lentiviral (Invitrogen, Inc., Carlsbad, Calif.), the Adenoviral Expression Systems (Invitrogen, Inc., Carlsbad, Calif.), the ADEASY™ XL Adenoviral Vector System (Stratagene, La Jolla, Calif.) and the VIRAPORT® Retroviral Gene Expression System (Stratagene, La Jolla, Calif.). Non-limiting examples of prokaryotic expression systems include the CHAMPION™ pET Expression System (EMD Biosciences-Novagen, Madison, Wis.), the TRIEX™ Bacterial Expression System (EMD Biosciences-Novagen, Madison, Wis.), the QIAEXPRESS® Expression System (QIAGEN, Inc.), and the AFFINITY® Protein Expression and Purification System (Stratagene, La Jolla, Calif.). Yeast expression systems include, without limitation, the EASY-SELECT™ *Pichia* Expression Kit (Invitrogen, Inc., Carlsbad, Calif.), the YES-ECHO™ Expression Vector Kits (Invitrogen, Inc., Carlsbad, Calif.) and the SPECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the BAC-TO-BAC® (Invitrogen, Inc., Carlsbad, Calif.), and the BD BACULOGOLD™ (BD Biosciences-Pharmigen, San Diego, Calif.). Insect expression systems include, without limitation, the *Drosophila* Expression System (DES®) (Invitrogen, Inc., Carlsbad, Calif.), INSECTSELECT™ System (Invitrogen, Inc., Carlsbad, Calif.) and INSECTDIRECT™ System (EMD Biosciences-Novagen, Madison, Wis.). Non-limiting examples of mammalian expression systems include the T-REX™ (Tetracycline-Regulated Expression) System (Invitrogen, Inc., Carlsbad, Calif.), the FLP-IN™ T-REX™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the EXCHANGER® System, INTERPLAY™ Mammalian TAP System (Strat-agene, La Jolla, Calif.), COMPLETE CONTROL® Inducible Mammalian Expression System (Stratagene, La Jolla, Calif.) and LAC-SWITCH® II Inducible Mammalian Expression System (Stratagene, La Jolla, Calif.).

Any suitable cells can be used to express the POI. In some embodiments, the cell is a mammalian cell. In certain embodiments the cell is a human cell. In some embodiments, the cell is a cancer cell. Examples of cancer cells include, but are not limited to, cells from a carcinoma, lymphoma, blastoma, sarcoma, and leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. In certain embodiments, the cell expressing the POI is a HEK293 cell.

III. THE CATCH AND RELEASE BIOPANNING PROCESS

A. The Catch and Release Biopanning for a Protein of Interest with Exogenous Protease Cleavage Site The subject methods provided herein allow for the generation of antibodies and binding proteins to a protein of interest (POI). In some embodiments, the POI is an extracellular or cell surface target antigen (single/multi-domains or full-length) with a cell protease cleavage site such as TEV protease. In other embodiments, the POI is an intracellular POI.

The TEV protease (also called Tobacco Etch Virus nuclear inclusion an endopeptidase) is a highly sequence-specific cysteine protease from Tobacco Etch Virus (TEV) that is a member of the PA clan of chymotrypsin-like proteases. Due to its high sequence specificity, TEV protease is used for the controlled cleavage of fusion proteins in vitro and in vivo. This specificity allows for the controlled cleavage of proteins when the preference sequence is inserted into flexible loops. It also makes it relatively non-toxic in vivo as the recognized sequence scarcely occurs in proteins. The protease recognition site is a seven amino acid consensus sequence is Glu-X-X-Tyr-X-Gln/Ser. In certain embodiments, the cleavage site is surface exposed. In some embodiments, the TEV protease recognition site is placed between 2 domains.

Cleavage occurs between the conserved Gln and Ser residues. X can be various amino acyl residues but note that not all residues are tolerated. A detailed analysis of altered cleavage sites is described in Dougherty et al., 1989, Virology 171:356-364, which is incorporated in its entirety herein and particularly for its teaching of altered cleavage sites.

The catch and release biopanning depicted in FIG. 1, illustrates different steps of generating monoclonal antibodies. The protein of interest is expressed as a Type 1 secreted membrane protein with an exogeneous protease cleavage site, e.g., TEV protease site, engineered between the POI and the single transmembrane domain; mammalian cells are transfected (either transiently or stably) with the construct and selected. Cells are exposed to a library of phage displaying a naïve binding partner such as randomized antibodies. These phages are allowed to bind and non-binding phage washed away. Cells are then exposed to TEV protease to cleave away the POI and any bound phage. Phage is then propagated and this process (biopanning) is repeated for typically several rounds. At the end of this process, phage are sequenced to characterize the nature of the binding partner and determine the structure of generated monoclonal antibodies.

Figure 2:
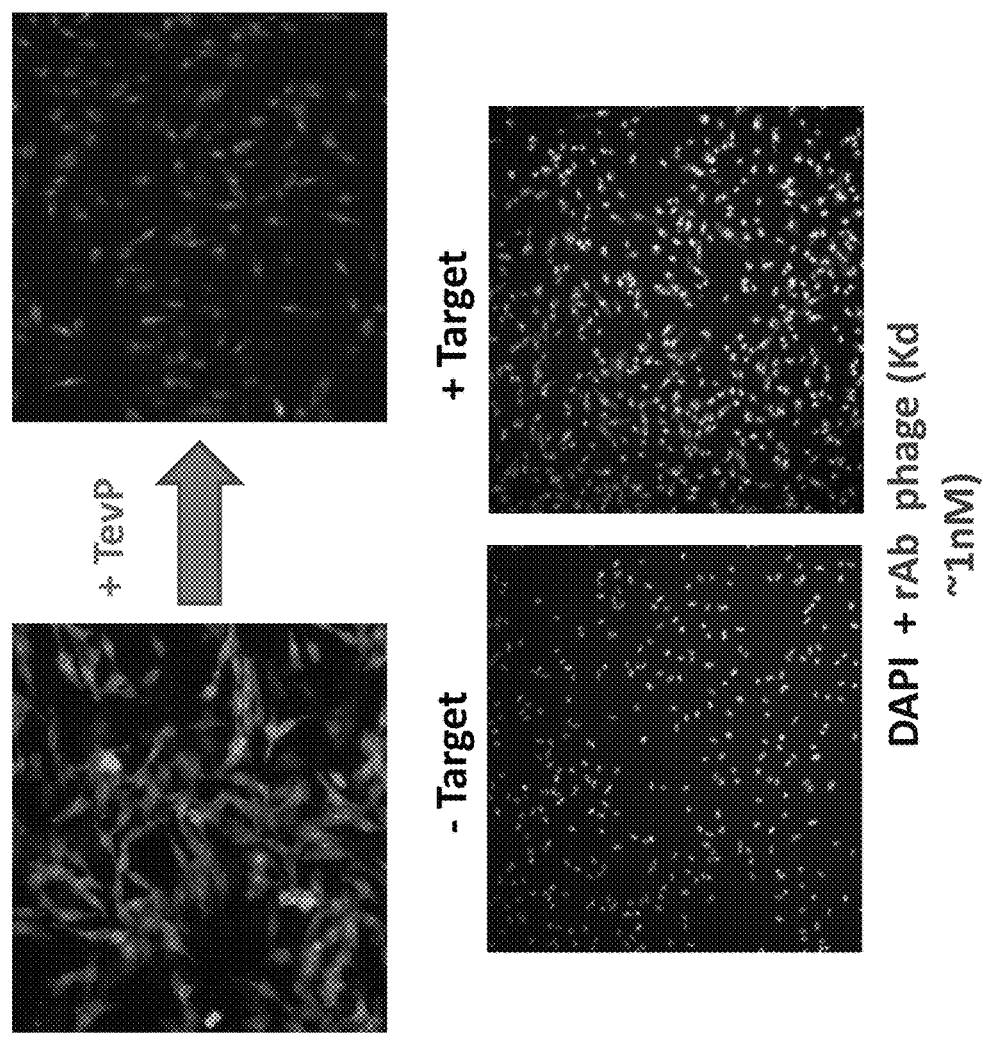
FIG. 2 illustrates the design of an exemplary biopanning as embodied by the subject methods provided herein, with cell expressing GFP-TEV-TM construct treated with TEV protease.

One of the exemplary biopanning embodied by the present invention is with cell expressing GFP-TEV_TM construct and treated with TEV protease, FIG. 2. FIG. 2 shows that TEV protease can effectively release the GFP protein from the cell surface. The bottom panel shows phage that are selected by the catch and release method generating a high affinity antibody (Kd=1 nM) will selectively bind to cells expressing the GFP-TEV-TM (right) but not to parental cells not expressing the GFP-TEV-TM. Table 1 summarizes the binding affinities and CDR sequences of a few anti-GFP clones identified through this process.

B. The Catch and Release Biopanning for a Protein of Interest with Endogenous Protease Cleavage Site Regulated cell-surface proteolysis underpins key processes of cellular growth and motility in both physiological and pathological contexts. However, comprehending how multiple proteolytic events cohesively integrate to yield context-dependent cellular behavior remains a challenge in the fields of both protease biology and systems biology in general. To address that challenge, a quantitative investigation was carried out on the integrated effect of multiple diverse proteolytic events and their interaction with cell-signaling pathways with respect to A Disintegrin and Metalloproteinases (ADAMs). ADAMs have been studied for decades as the principal cell-surface "sheddases" responsible for cleaving growth factor ligands and receptor tyrosine kinase domains from the cell surface. However, activity regulation, feedback, and catalytic promiscuity impede the understanding of context-dependent sheddase function, and clinical trials targeting metalloproteinases in cancer have failed, in part, due to a poor understanding of the complex functions they mediate. Using a combined paradigm for

TABLE 1

| Antigen | Fab | L3 | H1 | H2 | H3 | Affinity |
|---|---|---|---|---|---|---|
| GFP | A5 | YVSYYLF (SEQ ID NO: 18) | ISYSYM (SEQ ID NO: 19) | SIYPSYSYTS (SEQ ID NO: 20) | GSAL (SEQ ID NO: 21) | ~1 nM |
|  | A7 | SWGLI (SEQ ID NO: 22) | ISYYSI (SEQ ID NO: 23) | SIYPYYSSTS (SEQ ID NO: 24) | AGWVASSGM (SEQ ID NO: 25) | ~1 nM |
|  | G3 | SSSGASPI (SEQ ID NO: 26) | LSSSYI (SEQ ID NO: 27) | SIYPYSSYTY (SEQ ID NO: 28) | VPYYHYYSYPGW VPGYGM (SEQ ID NO: 29) | ~10 nM |
|  | R3.1 | ASGPF (SEQ ID NO: 30) | LSSSI (SEQ ID NO: 31) | SIYSSSSYTS (SEQ ID NO: 32) | YWAAL (SEQ ID NO: 33) | <1 nM |

Figure 3:
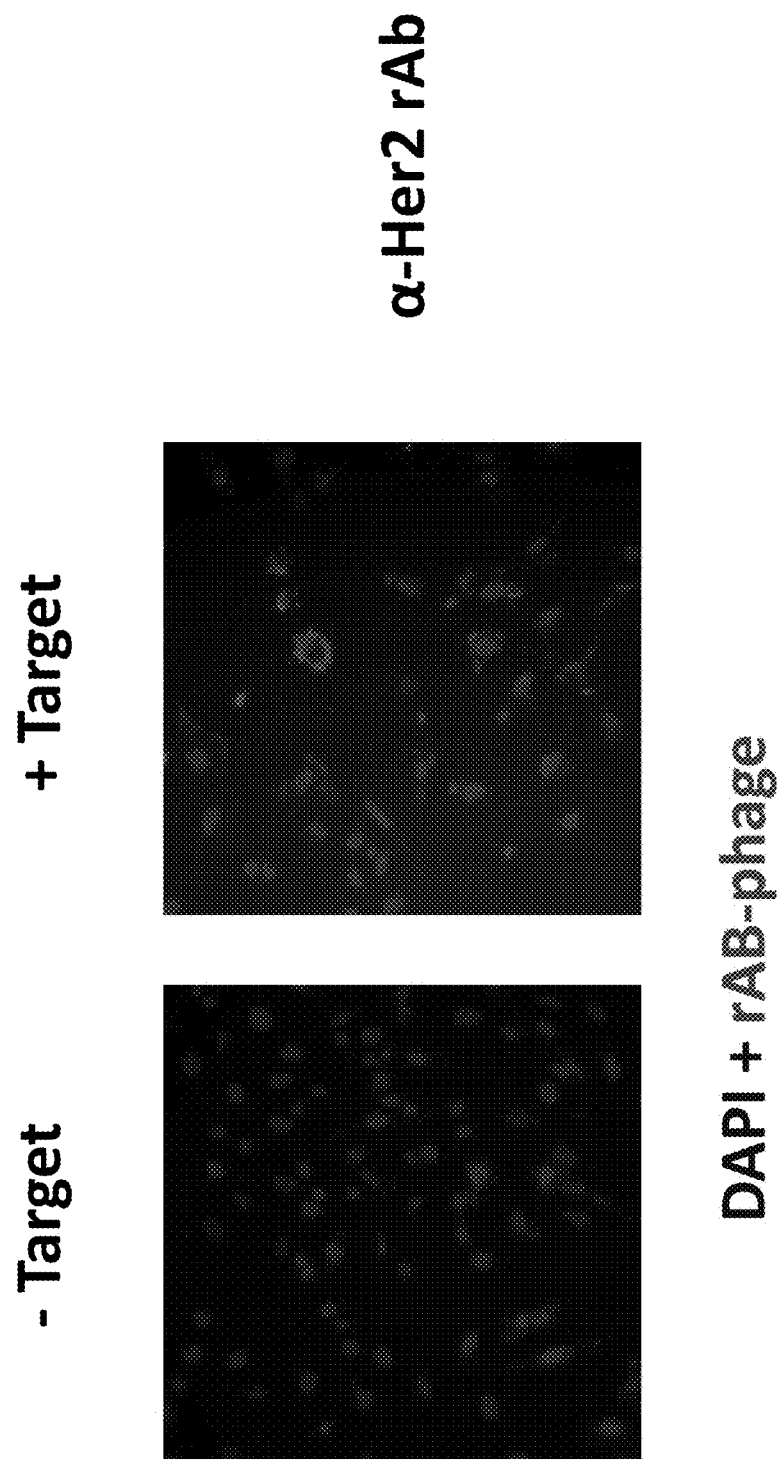
FIG. 3 illustrates an exemplary biopanning wherein the protein of interest contains α-Her2 with a TEV protease cleavage site.
Figure 4:
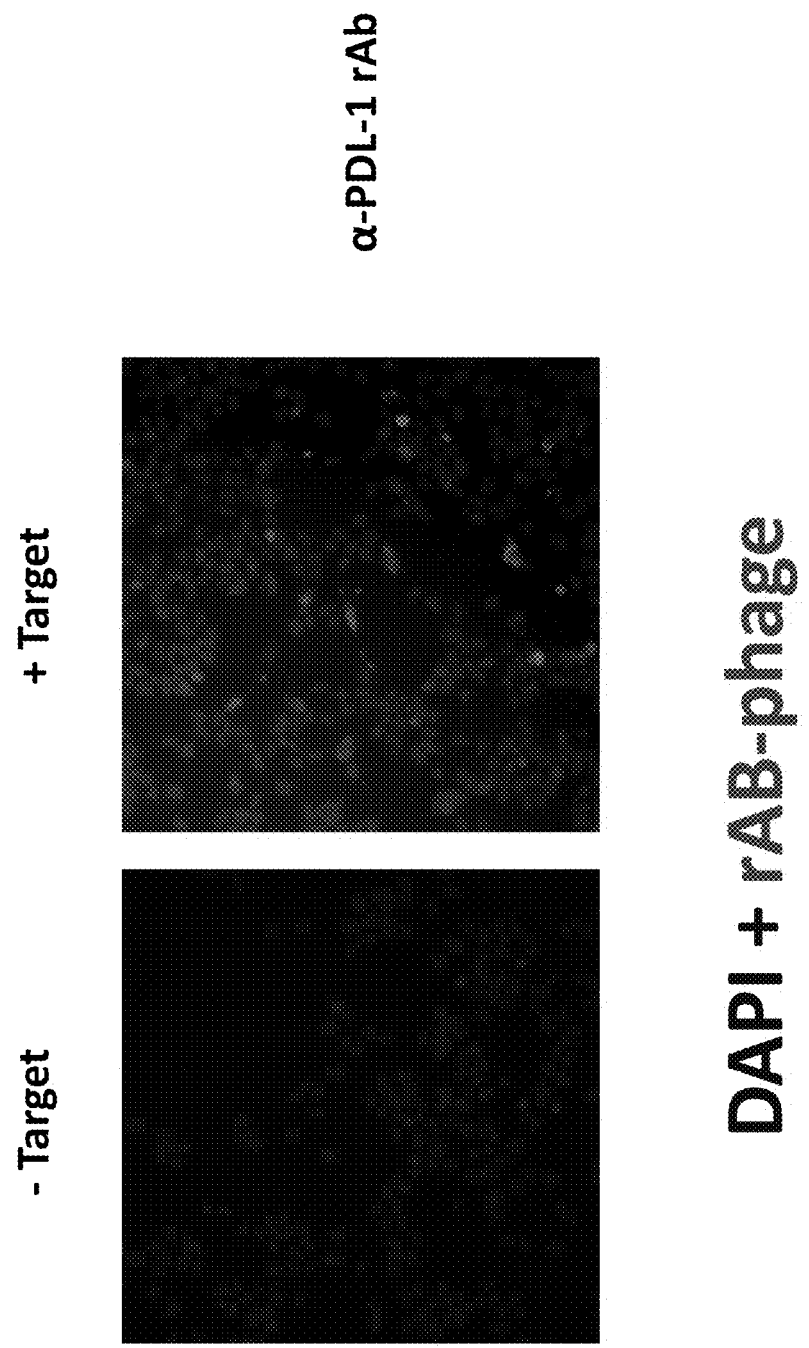
FIG. 4 illustrates an exemplary biopanning wherein the protein of interest contains PDL-1 with a TEV protease cleavage site.

In some embodiments, antigens provided in this invention are important in cancer therapeutics, for example Her2 receptor and PDL-1 receptor. As illustrated in FIG. 3, cells expressing the Her2 antigen generated antibody-phage that bind to the Her2 expressing cells but not the parental cells. Similar results were seen for cells expressing the PDL-1 ligand that selected phage bound to cells expressing the PDL-1 and not to parental cells illustrated in FIG. 4. Antibodies that are expressed by such phages show high affinity for Her2 receptor and PDL-1 as shown in FIG. 5.

This technology has been expanded to "mutiple-pass" transmembrane anchors, each containing a TEV protease site on the extracellular portions which allows the selection for binding partners for loops from GPCR receptors. In this embodiment, extracellular loops from multi-pass transmembrane proteins are displayed on cells, phage are allowed to bind and bound phage-antibody-antigen complexes are released by cleaving with exogenous protease, for example TEV protease.

In some embodiments, the catch and release biopanning can be used for screening combinatorial polypeptide libraries. In certain embodiments, a eukaryotic host is used that alleviates expression biases present in bacterially propagated combinatorial libraries An expectation is that rare peptides will be capable of interfering with intracellular signaling systems in interesting and novel ways. Using catch and release biopanning can lead to reagents such as antibodies or polypeptides that can be used to understand function of biological pathways and discern new drug candidates.

monitoring and analyzing complex networks of protease activities that interface with signaling pathways to influence cellular migration in the invasive diseases of cancer and endometriosis, it was determined that sheddase activity integrates with signaling pathways to direct cell migration, especially through concomitant proteolysis of both ligands and receptors. The indirect reduction of sheddase activity through kinase inhibition can lead to an accumulation of growth-factor receptors on the cell surface, consequently producing undesired compensatory signaling feedback. Given the large number of possible protease combination at hand, such efforts and their therapeutic counterparts would benefit from a quantitative, system level comprehension of overall protease network behavior to inform experimentation and therapeutic design.

In some embodiments the "sheddases" cleavage site sequence can be engineered into the POI, where the specific sheddase is naturally not expressed in the specific cell line or the specific sheddase is silenced (knocked-down) or totally knocked-out (KO). Catch and release biopanning is then performed to generate antibodies or polypeptides occurs similarly to the method used with protease cleavage site using exogenous protease cleavage site described herein.

In some embodiments, the present subject methods includes the use of a sheddase cleavage site to identify substrates of a specific sheddase in conjunction with catch and release biopanning to generate specific antibodies or polypeptides that bind to the identified specific sheddase substrates. In certain embodiments, cells harboring the sheddase will be knocked out for sheddase function by any of a variety of means known to ordinary skilled in the art (e.g., using siRNA or CRIPSR/Cas system reagents). Next, phage libraries expressing antibodies or polypeptides are contacted with the cells. Cells are washed to remove any unbound phage. Washed cells with bound phages are then treated with purified sheddase to cleave the endogenous substrates from the cell membrane. After several rounds of selection and enriching for phage that express antibodies that bind to the sheddase substrates, the antibodies are purified using standard mass spectrometry pull-down methods to identify the sheddase substrate bound to the antibody. Phage clones are subsequently analyzed to identify the antibodies that bind to the sheddase susbtrates.

IV. EXAMPLES

Example 1

Vector Construction

A series of mammalian transient expression vectors along with compatible retroviral producing vectors for generating stable cell lines. FLAG tagged target antigens (PCR-amplified or synthetic gene assembly) were cloned with NdeI and BamHI into a modified pcDNA3.1 backbone containing a C-terminal TEV protease cleavage site flanked by flexible Gly-Ser linkers (GSGGS-TevS-GGGGS) SEQ ID NO: 34 followed by the PDGF single pass TM domain-UnaG (Kumagai A, et al., 2013, Cell 153(7):1602-1611). For fluorescent imaging of transfected cells, backbones carry either C-terminal UnaG, GFP, or mCherry fusions. For non-cleavable antigens, the Tev site was omitted from the Gly-Ser linker. A dual anchor vector was created for displaying antigen loops or flexible N-terminal domains of multi-pass membrane proteins by cloning target antigens (NdeI and BamHI) between an N-terminal Transferrin receptor TM and C-terminal PDGF TM-UnaG domain. Flexible Gly-Ser linker-Tev sites flank the cloned antigen loops so that proteolysis of the dual TEV sites release the intervening polypeptide. The same cloning cassettes were introduced into a pQCXI retroviral backbone (Clontech) containing a Blasticidin resistance gene for selecting stable integrants following viral transduction of target cell lines. All restriction enzymes and DNA polymerases were purchased from NEB (Ipswich, Mass.). Oligonucleotides and gBlocks Gene Fragments were purchased from IDT and all constructs were verified by DNA sequencing (Quintara Biosciences).

Example 2

Cell Lines

Human embryonic kidney 293 (HEK293) and HeLa cell lines were cultured at 37° C., 5% $CO_2$ in Dulbecco's modified Eagle's medium (DMEM, Thermo Scientific) supplemented with 10% (v/v) fetal bovine serum (FBS, Gibco), 4 mM/L L-Glutamine, sodium pyruvate, penicillin/streptomycin (Pen/Strep, 100 U/mL). The 293-GPG retrovirus packaging cell line (Ory D S, Neugeboren B A, & Mulligan R C (1996) A stable human-derived packaging cell line for production of high titer retrovirus/vesicular stomatitis virus G pseudotypes. Proceedings of the National Academy of Sciences of the United States of America 93(21): 11400-11406) was cultured in DMEM, 10% FBS, 1 μg/mL tetracycline, 2 μg/mL puromycin, 300 μg/mL G418 at 37° C., 5% $CO_2$.

Example 3

Expression of Antigens and Cleavage by TEV Protease

HeLa cells (0.4×106/well) were seeded into a 6-well plate 24 h prior to transfection. On the day of transfection, the medium was replaced with Opti-MEM (Gibco) before cells were transfected with 4 μg pcDNA-antigen vector using Lipofectamine 2000 (Invitrogen) according to the manufacturer's protocol. Expression of extracellular localized antigens was confirmed by wide field epi-fluorescence microscopy. Proteolytic cleavage of displayed antigens was assessed in these cells with a dilution series of TEV protease in PBS (1, 10, 25, 50, and 100 μg/mL). Cells were washed once with PBS then 1 mL of TEV protease dilution was added and incubated for 5 min at 20° C., washed once with PBS and cells visualized by epi-fluorescence to assess the extent of extracellular cleavage. In the case of 12-well plates, a volume of 0.5 mL of protease was used to perform the cleavage reactions.

Example 4

Retrovirus Transduction

Virus production was performed by seeding 0.4×106 293-GPG cells per antigen in a 6-well plate 24 h prior to transfection. On the day of transfection, the medium was replaced with Opti-MEM (Gibco) before cells were transfected with 4 μg retroviral vector using Lipofectamine 2000 (Invitrogen) according to the manufacturer's protocol. Six hours post-transfection, the medium was replaced with DMEM supplemented with 10% FBS and Pen/Strep before incubating at 37° C., 5% CO2. Viral supernatants were harvested at 48 and 72 h post-transfection, filtered (0.45 μm Millex H V, Millipore) and applied to 0.2×106 target cells (HeLa or HEK293) in a 6-well plate and incubated overnight at 37° C., 5% CO2. Following the second viral transduction, target cells were removed with 0.05% Trypsin/EDTA and transferred to 15 $cm^2$ dishes and grown in DMEM, 10% FBS, Pen/Strep for 24 h prior to selection in Blasticidin (5 μg/mL) containing medium. Selection medium was replaced once per week with fresh Blasticidin-DMEM media until drug resistant foci (colonies) appeared. Stably integrated cells were expanded; frozen stocks were made and stored in LN2 before FACS sorting antigen-expressing cells via flow cytometry.

Example 5

FACS Analysis and Cell Sorting

Briefly, cells were completely dissociated in Versene (0.04% EDTA), washed once with phosphate-buffered saline (PBS) by centrifugation at 300 g for 5 min, then resuspended in 0.5 mL Opti-MEM, passed through a 40 μm nylon mesh cell strainer (Fisher Scientific) into a 5 mL round-bottom tube (BD Biosciences) and placed on ice. Cell sorting and analysis was carried out using a FACS Aria II flow cytometer (BD Biosciences) and BD FACSDiva software. The sort gate was a combination of the wild-type live cell gate (from FSC-H vs. SSC-H dot plot) and the events in the top 25% fluorescence (from the FITC histogram) determined for 10,000 events using a 488 nm wavelength. Fluorescent cells were collected in Opti-MEM and expanded in DMEM, 10% FBS, Pen/Strep, 1 μg/mL blasticidin before preparing frozen stocks.

Example 6

Fluorescence Imaging

Live cell wide field epifluorescent imaging was performed on a Zeiss Axio Ovserver.Z1 inverted microscope equipped with an X-Cite 120Q excitation light source using an Axio-Cam MRm camera and Zen Pro 2011 software (Carl Zeiss). Immuno-fluorescent (IF) binding assay of individual phage clones was performed on an IN Cell Analyzer 2000 high-content analysis system (GE Healthcare). Briefly, 10,000 antigen expressing cells were seeded into a clear 96w flat-bottom tissue culture plate one day before imaging. On the day of imaging, cells were washed once with PBS and 100 µL of purified individual phage clones in binding buffer were incubated with cells for 1 h at 20° C. Phage solutions were decanted, wells washed three times with PT buffer (PBS, 0.05% Tween 20) and fixed with 1% formaldehyde in PBS for 15 min at 20° C. After cell fixation, mouse anti-M13 phage primary antibody (1:500 in PBT, GE Healthcare) was added for 30 min at 37° C., followed by three washes with PT buffer before adding Alexa Fluor 546 Goat anti-Mouse IgG secondary antibody (1:500 in PBT, Invitrogen) for 30 min at 37° C. Nuclei were stained with Hoechst 33342 (2 µg/mL in PBT), cells were washed three times with PT buffer and placed in PBS for imaging.

Example 7

Phage Library and Catch and Release Selections

A limited diversity phage display library (gift from Sachdev Sidhu, University of Toronto, Toronto, ON, Canada) enriched for serine and tyrosine in complementarity determining regions (CDRs) was used for all selections (Fellouse F A, et al., 2007, Journal of Molecular Biology 373(4):924-940; Persson H, et al., 2013, Journal of Molecular Biology 425(4):803-811). One day before selections, antigen target cell lines are seeded into 12-well plate (0.2×106 cells/well) and grown overnight in DMEM, 10% FBS, Pen/Strep. The next day, 0.25 mL of phage library per antigen (125× diversity) was precipitated with PEG/NaCl and resuspended in 1 mL Binding Buffer (DMEM, 10% FBS, 50 mM Hepes) before being added to each well of antigen target cells. Phage was incubated with cells for 2 h, washed with 2 mL of PBS supplemented with 0.1 g/L each of $CaCl_2$ and $MgCl_2$ (PBS+) with gentle rocking for 5 minutes. The wash step was repeated a total of 5 times. For less stringent washes, 2 mL PBS+ was added to all wells and immediately aspirated (10-15 s per wash step); these washes were repeated 3-5 times. Bound phage was eluted by addition of 0.5 mL Tev protease (30-50 µg/mL) in PBS+ for 5 min and Tev cleaved phage was propagated in *Escherichia coli* XL1-blue (Stratagene) with the addition of M13-K07 helper phage (New England Biolabs). After growth overnight at 37° C., phage were concentrated by precipitation with PEG/NaCl and resuspended in PBT buffer (PBS, 0.5% (w/v) bovine serum albumin (BSA), 0.1% (v/v) Tween 20 (Sigma-Aldrich)), as described (Weiss G A, Watanabe C K, Zhong A, Goddard A, & Sidhu S S (2000) Rapid mapping of protein functional epitopes by combinatorial alanine scanning. Proceedings of the National Academy of Sciences of the United States of America 97(16):8950-8954). For targets expressed on HEK293 cells, selections were carried out in solution with phage binding and wash steps incubated on a rotating rack and cells pelleted (30 s at 3000 rpm) prior to removal of supernatant and addition of next reagent. A total of four rounds of selection were performed for each antigen and individual phage clones were analyzed from either the third or fourth round of selection. This selection strategy could be scaled down to a 96-well microtiter plate format or in solution (binding cells to paramagnetic beads) to increase throughput and reduce the amount of reagents used for panning and elution steps.

Example 8

Sheddase Release Selections

Target cells lines expressing sheddase substrates are incubated with phage library for 1-2 h at 20° C. Unbound phage are washed away with PBS+ buffer (3-5 times) before antigen-bound phage is selectively eluted by addition of exogenous sheddase for 5-10 min at 20° C. If the sheddase to be used is endogenously present in the target cell line, cells are treated with specific sheddase small-molecule inhibitors or expression of the sheddase will be knocked down via siRNA transfection prior to performing phage display selections. Selectively released phage are propagated overnight in XL1-Blue cells, concentrated by precipitation with PEG/NaCl and resuspended in PBT buffer. For each specific sheddase, four to five rounds of selection will be performed before analyzing individual phage clones.

Example 9

Expression and Purification of Fab Clones

Fabs clones were PCR-amplified from phage supernatants and cloned into an in-house protein expression vector pJK5 (Koerber J T, Thomsen N D, Hannigan B T, Degrado W F, & Wells J A (2013) Nature-inspired design of motif-specific antibody scaffolds. Nature biotechnology 31(10):916-921) containing an SfiI cloning cassette encoding a C-terminal biotin-acceptor peptide and co-expressed BirA gene to enzymatically biotinylate each Fab. Selected Fabs were expressed in a protease deficient C43 (DE3) strain (Thomsen N D, Koerber J T, & Wells J A (2013) Structural snapshots reveal distinct mechanisms of procaspase-3 and -7 activation. Proceedings of the National Academy of Sciences of the United States of America 110(21):8477-8482), purified by Protein A chromatography and stored at 4° C. (short-term) or flash frozen in 10% glycerol for long-term storage at −80° C. Briefly, C43 cells were transformed with expression plasmids and grown in TB media supplemented with 0.4% glycerol. Protein expression was induced with 1 mM IPTG at an OD600 of 0.8, and 50 µM biotin was added to the media before incubation overnight at 30° C. with shaking at 200 rpm.

Example 10

Selection of Antibodies to Ras-Induced Antigens in HEK293 Cells

Figure 7:
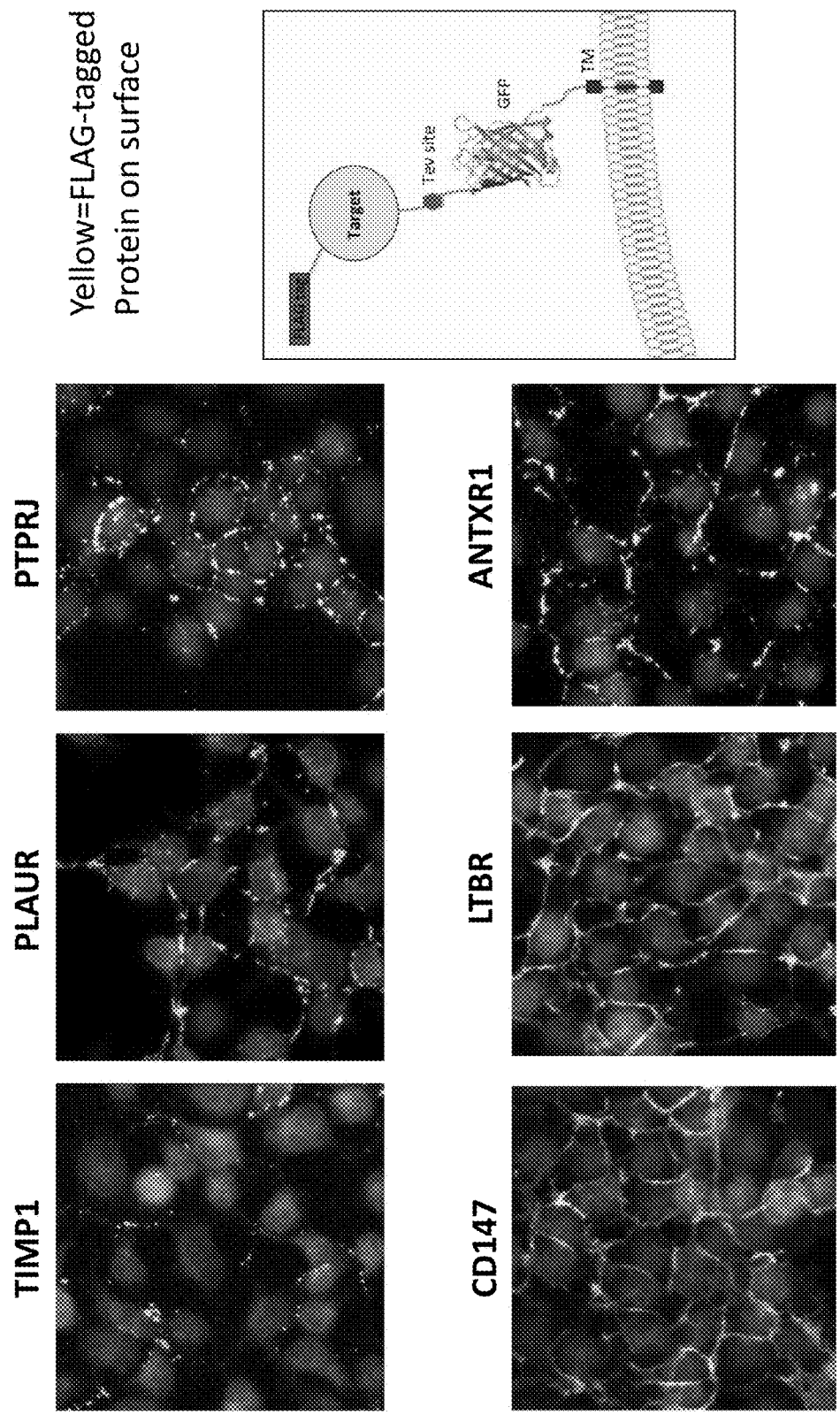
FIG. 7 shows the stable of expression of proteins of interest TIMP1, PLAUR, PTPRJ, CD147, LTBR and ANTXR1 in HEK293 cells.
Figure 8:
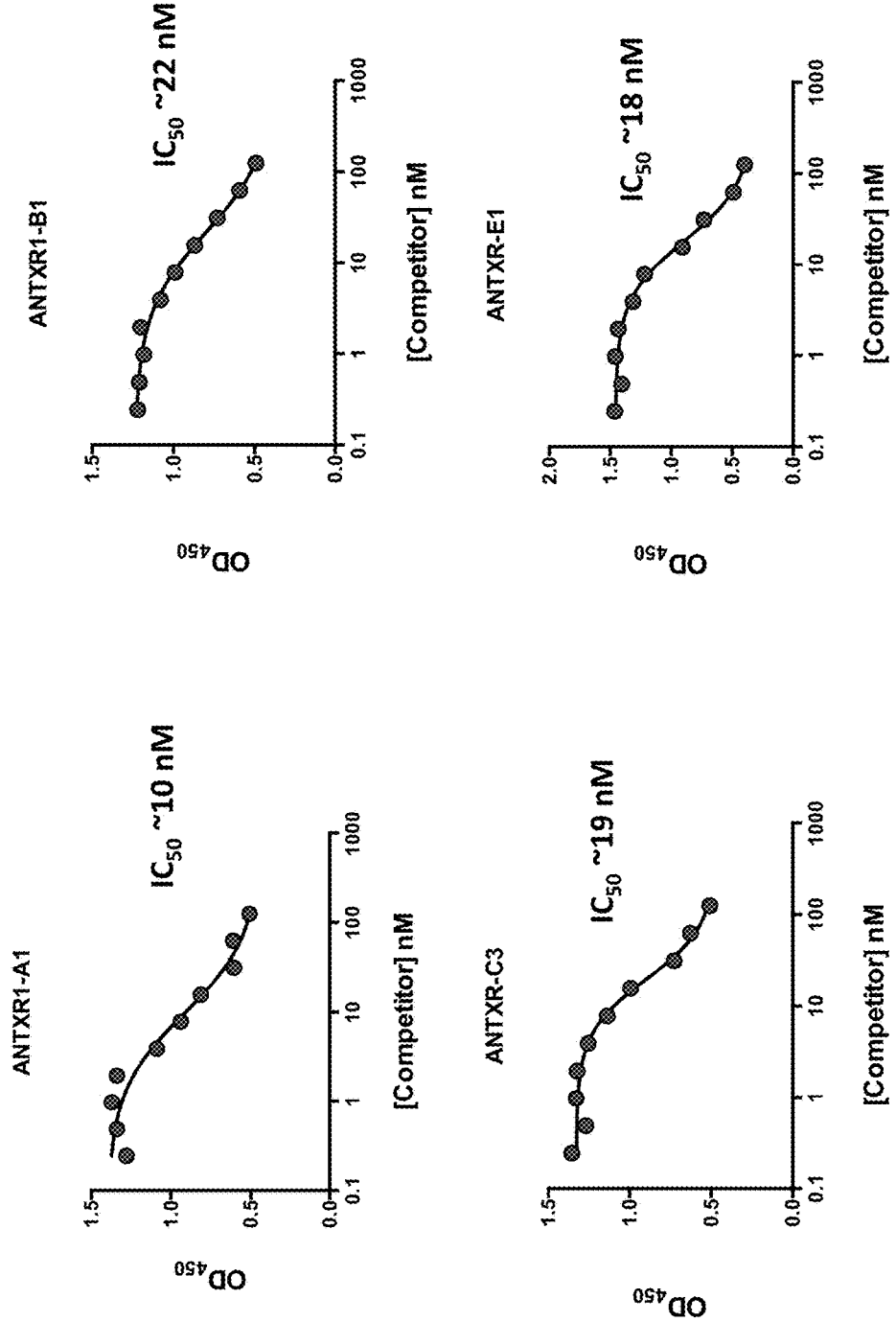
FIG. 8 includes graphs showing that antibodies selected for binding to ANTXR1 using the subject methods exhibit high affinity antigen binding.
Figure 9:
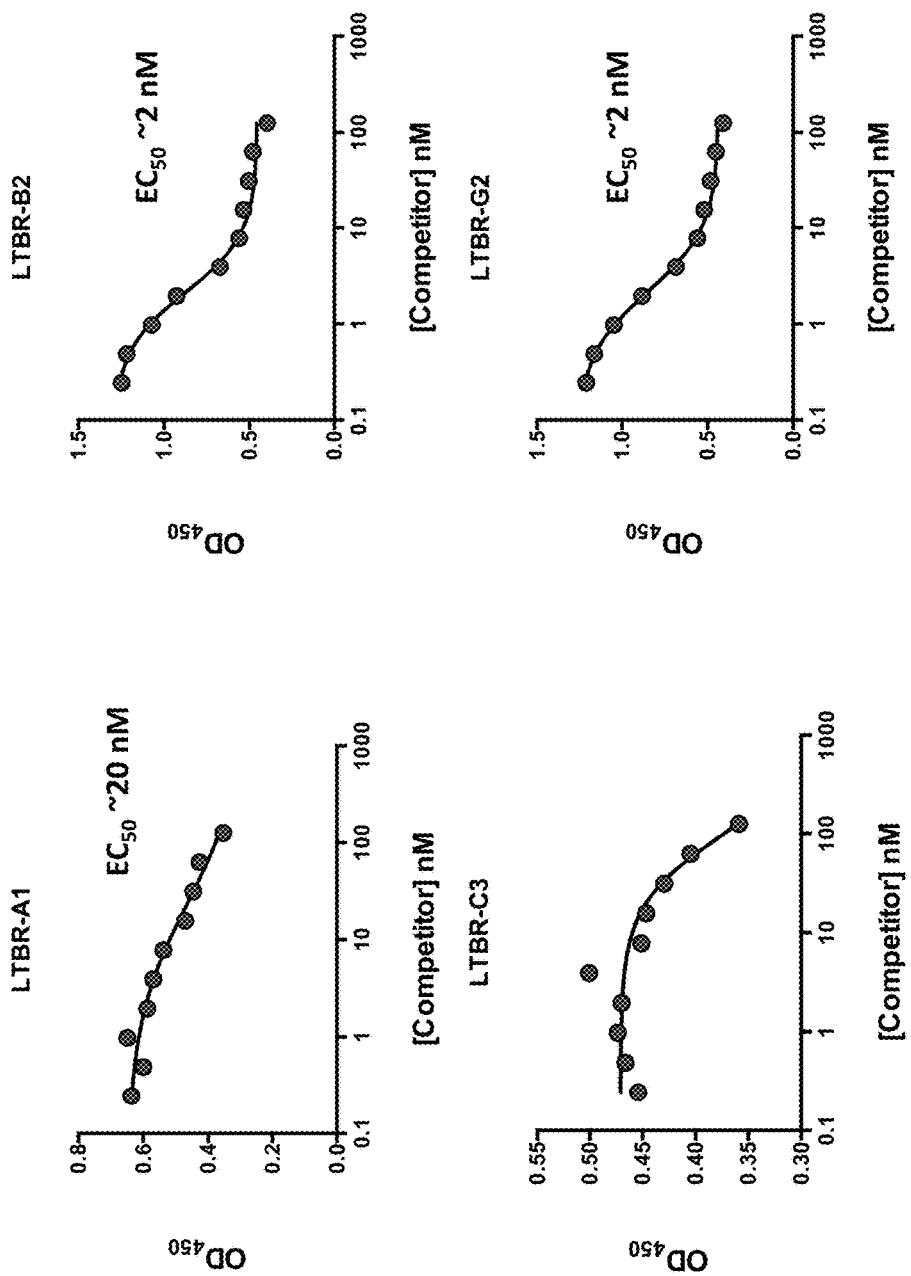
FIG. 9 includes graphs showing that antibodies selected for binding to LTBR using the subject methods exhibit high affinity antigen binding.
Figure 10:
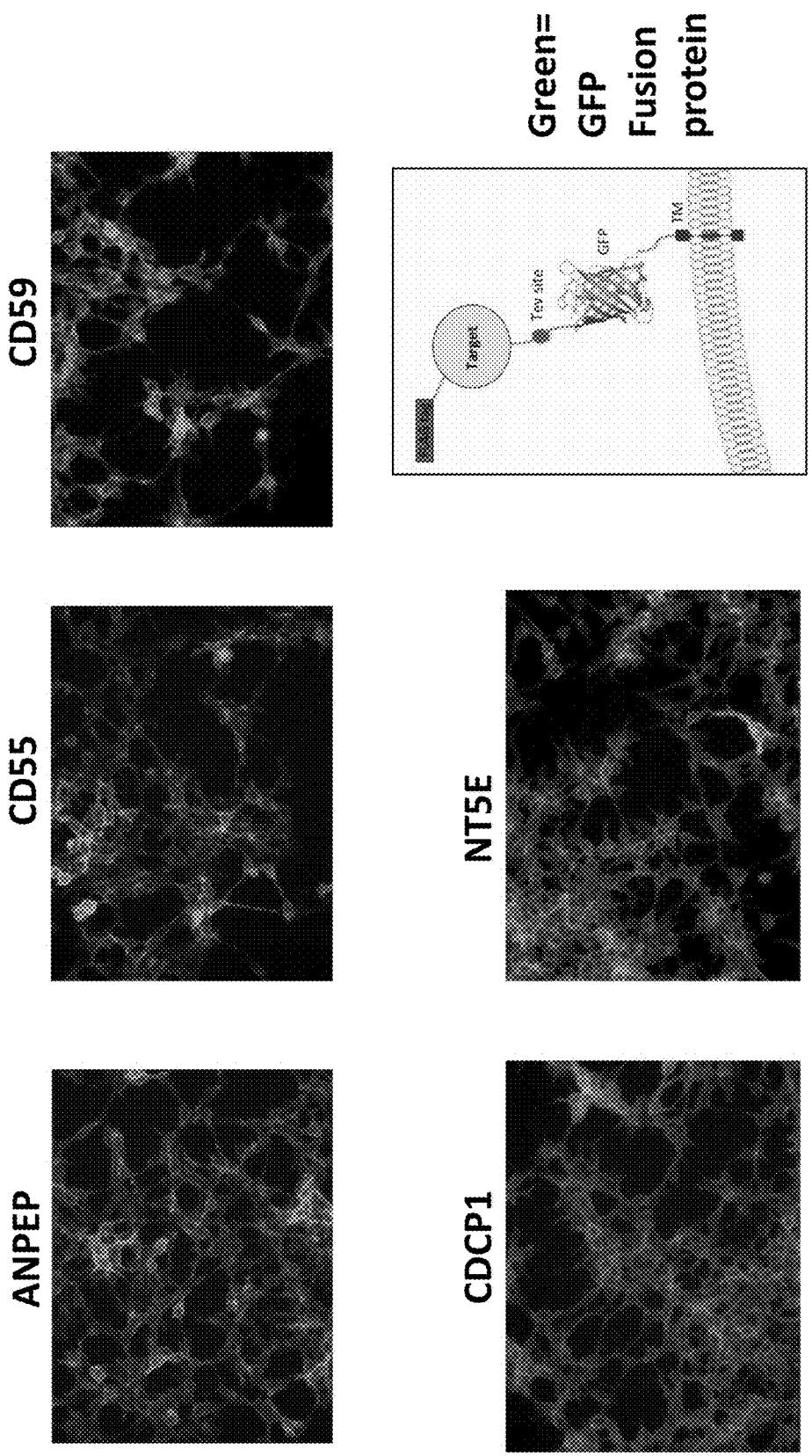
FIG. 10 shows additional stable cell lines generated that express Ras-induced antigens.

The subject methods were used to select for antibodies that bind to protein of interest antigens that exhibited Ras-induced expression in Human Embryonic Kidney (HEK) 293 cells. POI constructs included an extracellular FLAG tag and GFP site as shown in FIG. 7. HEK293 cells that stably expressed TIMP1, PLAUR, PTPRJ, CD147 LTBR, and ANTXR1 were made using methods similar to those described in Example 3. Similar cell lines that stably expressed Ras-induced ANPEP, CD55, CD59, CDCP1, and NTSE were also made (FIG. 10). An exemplary expression vector for expressing a protein of interest (LBTR antigen) is shown below (SEQ ID NO:1). A library of phage-antibody constructs were prepared as outlined in Example 7 and contacted with each cell line. Cells were subsequently washed to remove unbound phage and contacted with TEV protease to release antibody-antigen complexes. Antibody-antigen complexes were isolated and phage from the antibody-antigen complexes were isolated. The biopanning steps were repeated for 4 more rounds. As shown in FIGS. 8 and 9, antibodies selected exhibited high affinity for ANTXR1 (FIG. 8) and LTBR (FIG. 9). Sequences of exemplary isolated antibodies that bind to ANTXR1 and LTBR are shown below.

TABLE 2

|  | Sample | Plate ID | LC | HC1 | HC2 | HC3 |
|---|---|---|---|---|---|---|
| ANTZR1R3 Binders | 1 | A1 | SYGLF (SEQ ID NO: 35) | LYSSSM (SEQ ID NO: 36) | SIYSYYGYTY (SEQ ID NO: 37) | HWAL (SEQ ID NO: 38) |
|  | 2 | B1 | SYYLI (SEQ ID NO: 39) | LSSYYI (SEQ ID NO: 40) | YISPYSGYTS (SEQ ID NO: 41) | YWAL (SEQ ID NO: 42) |
|  | 3 | C3 | SYYLI (SEQ ID NO: 39) | ISYSSI (SEQ ID NO: 43) | SIYPYYGYTY (SEQ ID NO: 44) | HWGM (SEQ ID NO: 45) |
|  | 4 | E1 | SFYLI (SEQ ID NO: 46) | LYYSSM (SEQ ID NO: 47) | SIYPYYGYTY (SEQ ID NO: 44) | YWAF (SEQ ID NO: 48) |
|  | 5 | G1 | SYYLI (SEQ ID NO: 39) | FSSSSI (SEQ ID NO: 49) | SIYPYYGYTY (SEQ ID NO: 44) | SWGM SEQ ID NO: 50) |
| LTBRR3 Binders | 6 | A1 | SSYSLI (SEQ ID NO: 51) | FSSSSI (SEQ ID NO: 49) | SIYPSYGYTY (SEQ ID NO: 52) | PAGYFWGSSWFWGF (SEQ ID NO: 53) |
|  | 7 | B2 | SWGVAYPI (SEQ ID NO: 54) | IYSSSM (SEQ ID NO: 55) | SISSYSSYTS (SEQ ID NO: 56) | SFYSAM (SEQ ID NO: 57) |
|  | 8 | C3 | PGYHLI (SEQ ID NO: 58) | LSYYSM (SEQ ID NO: 59) | SIYSSYGYTY (SEQ ID NO: 60) | WYGFYVGHGSYAM (SEQ ID NO: 61) |
|  | 9 | G2 | SSYSLI (SEQ ID NO: 51) | IYSYSM (SEQ ID NO: 62) | YIYPSYGSTY (SEQ ID NO: 63) | WYWWYGGSGSGYAM (SEQ ID NO: 64) |

POI Construct Vector:
(SEQ ID NO: 1)

GACGGATCGGGAGATCTCCCGATCCCCTATGGTGCACTCTCAGTACAATCTGCTCTG

ATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGAGAT

CTCTGCAGCCCCGATAAAATAAAAGATTTTATTTAGTCTCCAGaAAAAGGGGGAAT

GAAAGACCCCACCTGTAGGTTTGGCAAGCTAGCTGCAGTAACGCCATTTTGCAAGGC

ATGGAAAAATACCAAACCAAGAATAGAGAAGTTCAGATCAAGGGCGGGTACATGA

AAATAGCTAACGTTGGGCCAAACAGGATATCTGCGGTGAGCAGTTTCGGCCCCGGC

CCGGGGCCAAGAACAGATGGTCACCGCAGTTTCGGCCCCGGCCCGAGGCCAAGAAC

AGATGGTCCCCAGATATGGCCCAACCCTCAGCAGTTTCTTAAGACCCATCAGATGTT

TCCAGGCTCCCCCAAGGACCTGAAATGACCCTGCGCCTTATTTGAATTAACCAATCA

GCCTGCTTCTCGCTTCTGTTCGCGCGCTTCTGCTTCCCGAGCTCTATAAAAGAGCTCA

CAACCCCTCACTCGGCGCGCCAGTCCTCCGACAGACTGAGTCGCCCGGGAATACGA

CTCACTATAGGGAGACCCAAGCTGGCTAGTTATCGATTAGTGCGGCCGCCACCATGG

AGACAGACACACTCCTGCTATGGGTACTGCTGCTCTGGGTTCCAGGTTCCACTGGTGACT

ACAAGGATGACGACGATAAGGGGGCCAGCTCGGCCCA*GCGGTGCCTCCATATGC*

*GTCGGAGAACCAGACCTGCAGGGACCAGGAAAAGGAATACTATGAGCCCCAGCACCG*

*CATCTGCTGCTCCCGCTGCCGCCAGGCACCTATGTCTCAGCTAAATGTAGCCGCATC*

*CGGGACACAGTTTGTGCCACATGTGCCGAGAATTCCTACAACGAGCACTGGAACTACC*

*TGACCATCTGCCAGCTGTGCCGCCCCTGTGACCCAGTGATGGGCCTCGAGGAGATTG*

*CCCCCTGCACAAGCAAACGGAAGACCCAGTGCCGCTGCCAGCCGGGAATGTTCTGTG*

-continued

*CTGCCTGGGCCCTCGAGTGTACACACTGCGAGCTACTTTCTGACTGCCCGCCTGGCAC*

*TGAAGCCGAGCTCAAAGATGAAGTTGGGAAGGGTAACA ACCACTGCGTCCCCTGCAA*

*GGCCGGGCACTTCCAGAATACCTCCTCCCCCAGCGCCGGCTGCCAGCCCCACACCAG*

*GTGTGAGAACCAAGGTCTGGTGGAGGCAGCTCCAGGCACTGCCCAGTCCGACACAAC*

*CTGCAAAAATCCATTAGAGCCACTGCCCCCAGAGATGTCAGGAACCATGCTG*ATGTC<u>G</u>

<u>GCCACCGGGGCC</u>GGATCCACTAGTGGGGGCTCCGGCTCCGAAAATCTCTACTTCCA

GAGTGGCAGCGGAGGCTCCGTGAGCAAAGGCGAAGAGCTGTTCACCGGCGTGG

TGCCCATCCTGGTGGAGCTGGACGGCGACGTGAACGGCCACAAGTTCAGCGTG

AGCGGCGAGGGCGAGGGCGACGCCACTACGGCAAGCTGACCCTGAACTGC

TGTGCACCACCGGCAAGCTGCCCGTGCCCTGGCCCACCCTGGTGACCACCCTG

GGCTACGGCGTGCAGTGCTTCGCCCGGTACCCCGACCACATGAAGCAGCACGA

CTTCTTCAAGAGCGCCATGCCCGAAGGCTACGTGCAGGAGCGGACCATCTTCT

TCAAGGACGACGGCAACTACAAGACCCGGGCCGAGGTGAAGTTCGAGGGCGA

CACCCTGGTGAACCGGATCGAGCTGAAGGGCATCGACTTCAAGGAGGACGGCA

ACATCCTGGGCCACAAGCTGGAGTACAACTACAACAGCCACAACGTGTACATC

ACCGCCGACAAGCAGAAGAACGGCATCAAGGCCAACTTCAAGATCCGGCACAA

CATCGAGGACGGCGGCGTGCAGCTGGCCGACCACTACCAGCAGAACACCCCCA

TCGGCGACGGCCCCGTGCTGCTGCCCGACAACCACTACCTGAGCTACCAGAGC

GCCCTGTTCAAGGACCCCAACGAGAAGCGGGACCACATGGTGCTGCTGGAGTT

CCTGACCGCCGCCGGCATCACCGAGGGCATGAACGAGCTCTATAAGAGATCCG

GCGGAAGCGGTGGCGGTGGCAGC*GCCGTGGGCCAGGACACCCAGGAGGTGATC*

*GTGGTGCCCCACAGCCTGCCCTTCAAGGTGGTGGTAATCAGCGCCATCCTGGC*

*ACTGGTGGTGCTGACCATCATCAGCCTGATCATCCTGATTATGCTGTGGCAGAA*

*GAAGCCCA*GGTGAGAATTCTGCAGATATTCAGCACAGTGGGGGCCGCTCGAGTCTA

GAGGGCCCGTTTAAACCCGCTGATCAGCCTCGACTGTGCCTTCTAGTTGCCAGCCAT

CTGTTGTTTGCCCCTCCCCCGTGCCTTCCTTGACCCTGGAAGGTGCCACTCCCACTGT

CCTTTCCTAATAAAATGAGGAAATTGCATCGCATTGTCTGAGTAGGTGTCATTCTATT

CTGGGGGGTGGGGTGGGGCAGGACAGCAAGGGGGAGGATTGGGAAGACAATAGCA

GGCATGCTGGGGATGCGGTGGGCTCTATGGCTTCTGAGGCGGAAAGAACCAGCTGG

GGCTCTAGGGGGTATCCCCACGCGCCCTGTAGCGGCGCATTAAGCGCGGCGGGTGT

GGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAAT

CGGGGGCTCCCTTTAGGGTTCCGATTTAGTGCTTTACGGCACCTCGACCCCAAAAAA

CTTGATTAGGGTGATGGTTCACGTACCTAGAAGTTCCTATTCCGAAGTTCCTATTCTC

TAGAAAGTATAGGAACTTCCTTGGCCAAAAAGCCTGAACTCACCGCGACGTCTGTCG

AGAAGTTTCTGATCGAAAAGTTCGACAGCGTCTCCGACCTGATGCAGCTCTCGGAGG

GCGAAGAATCTCGTGCTTTCAGCTTCGATGTAGGAGGGCGTGGATATGTCCTGCGGG

TAAATAGCTGCGCCGATGGTTTCTACAAAGATCGTTATGTTTATCGGCACTTTGCATC

GGCCGCGCTCCCGATTCCGGAAGTGCTTGACATTGGGGAATTCAGCGAGAGCCTGA

CCTATTGCATCTCCCGCCGTGCACAGGGTGTCACGTTGCAAGACCTGCCTGAAACCG

```
-continued
AACTGCCCGCTGTTCTGCAGCCGGTCGCGGAGGCCATGGATGCGATCGCTGCGGCC

GATCTTAGCCAGACGAGCGGGTTCGGCCCATTCGGACCGCAAGGAATCGGTCAATA

CACTACATGGCGTGATTTCATATGCGCGATTGCTGATCCCCATGTGTATCACTGGCA

AACTGTGATGGACGACACCGTCAGTGCGTCCGTCGCGCAGGCTCTCGATGAGCTGAT

GCTTTGGGCCGAGGACTGCCCCGAAGTCCGGCACCTCGTGCACGCGGATTTCGGCTC

CAACAATGTCCTGACGGACAATGGCCGCATAACAGCGGTCATTGACTGGAGCGAGG

CGATGTTCGGGGATTCCCAATACGAGGTCGCCAACATCTTCTTCTGGAGGCCGTGGT

TGGCTTGTATGGAGCAGCAGACGCGCTACTTCGAGCGGAGGCATCCGGAGCTTGCA

GGATCGCCGCGGCTCCGGGCGTATATGCTCCGCATTGGTCTTGACCAACTCTATCAG

AGCTTGGTTGACGGCAATTTCGATGATGCAGCTTGGGCGCAGGGTCGATGCGACGC

AATCGTCCGATCCGGAGCCGGGACTGTCGGGCGTACACAAATCGCCCGCAGAAGCG

CGGCCGTCTGGACCGATGGCTGTGTAGAAGTACTCGCCGATAGTGGAAACCGACGC

CCCAGCACTCGTCCGAGGGCAAAGGAATAGCACGTACTACGAGATTTCGATTCCAC

CGCCGCCTTCTATGAAAGGTTGGGCTTCGGAATCGTTTTCCGGGACGCCGGCTGGAT

GATCCTCCAGCGCGGGGATCTCATGCTGGAGTTCTTCGCCCACCCCAACTTGTTTATT

GCAGCTTATAATGGTTACAAATAAAGCAATAGCATCACAAATTTCACAAATAAAGC

ATTTTTTTCACTGCATTCTAGTTGTGGTTTGTCCAAACTCATCAATGTATCTTATCATG

TCTGTATACCGTCGACCTCTAGCTAGAGCTTGGCGTAATCATGGTCATAGCTGTTTCC

TGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTC

ACTGCCCGCTTTCCAGTCGGGAAACCTGTCGTGCCAGCTGCATTAATGAATCGGCCA

ACGCGCGGGGAGAGGCGGTTTGCGTATTGGGCGCTCTTCCGCTTCCTCGCTCACTGA

CTCGCTGCGCTCGGTCGTTCGGCTGCGGCGAGCGGTATCAGCTCACTCAAAGGCGGT

AATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCT

CTCCTGTTCCGACCCTGCCGCTTACCGGATACCIGTCCGCCTTTCTCCCTTCGGGAAG

CGTGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTT

GAAGTGGTGGCCTAACTACGGCTACACTAGAAGGACAGTATTTGGTATCTGCGCTCT

GCTGAAGCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGCAGAAAAA

AAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTT

GGTCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGAGG

GCTTACCATCTGGCCCCAGTGCTGCAATGATACCGCGAGACCCACGCTCACCGGCTC
```

-continued

```
CAGATTTATCAGCAATAAACCAGCCAGCCGGAAGGGCCGAGCGCAGAAGTGGTCCT

GCAACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCAAGGCGA

GTTACATGATCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCAT

AATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAA

TACGGGATAATACCGCGCCACATAGCAGAACTTTAAAAGTGCTCATCATTGGAAAA

CGTTCTTCGGGGCGAAAACTCTCAAGGATCTTACCGCTGTTGAGATCCAGTTCGATG

TAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACG

GAAATGTTGAATACTCATACTCTTCCTTTTTCAATATTATTGAAGCATTTATCAGGGT

TATTGTCTCATGAGCGGATACATATTTGAATGTATTTAGAAAAATAAACAAATAGGG

GTTCCGCGCACATTTCCCCGAAAAGTGCCACCTGACGTC
```

Italics: IgKappa Signal Peptide:

(SEQ ID NO: 2)
ATGGAGACAGACACACTCCTGCTATGGGTACTGCTGCTCTGGGTTCCAGG
TTCCACTGGT

Bold: Flag Tag:

GACTACAAGGATGACGACGATAAG     (SEQ ID NO: 3)

Bold Italics: LTBR Antigen:

(SEQ ID NO: 4)
GCGGTGCCTCCATATGCGTCGGAGAACCAGACCTGCAGGGACCAGGAAAA

GGAATACTATGAGCCCCAGCACCGCATCTGCTGCTCCCGCTGCCCGCCAG

GCACCTATGTCTCAGCTAAATGTAGCCGCATCGGGACACAGTTTGTGCC

ACATGTGCCGAGAATTCCTACAACGAGCACTGGAACTACCTGACCATCTG

CCAGCTGTGCCGCCCCTGTGACCCAGTGATGGGCCTCGAGGAGATTGCCC

CCTGCACAAGCAAACGGAAGACCCAGTGCCGCTGCCAGCCGGGAATGTTC

TGTGCTGCCTGGGCCCTCGAGTGTACACACTGCGAGCTACTTTCTGACTG

CCCGCCTGGCACTGAAGCCGAGCTCAAAGATGAAGTTGGGAAGGGTAACA

ACCACTGCGTCCCCTGCAAGGCCGGGCACTTCCAGAATACCTCCTCCCCC

AGCGCCCGCTGCCAGCCCCACACCAGGTGTGAGAACCAAGGTCTGGTGGA

GGCAGCTCCAGGCACTGCCCAGTCCGACACAACCTGCAAAAATCCATTAG

AGCCACTGCCCCCAGAGATGTCAGGAACCATGCTG

Double Underline: Cloning Sites 1 and 2 (Pop Antigens In/Out):

GGCCAGCTCGGCC     (SEQ ID NO: 5)
and
GGCCACCGGGGCC    (SEQ ID NO: 6)

Bold Underline: Tev Protease Cleavage Site

GAAAATCTCTACTTCCAGAGT     (SEQ ID NO: 7)

Bold Double Underline: YPET (SEQ ID NO: 8)
GTGAGCAAAGGCGAAGAGCTGTTCACCGGCGTGGTGCCCATCCTGGTGGA

GCTGGACGGCGACGTGAACGGCCACAAGTTCAGCGTGAGCGGCGAGGGCG

AGGGCGACGCCACCTACGGCAAGCTGACCCTGAAGCTGCTGTGCACCACC

GGCAAGCTGCCCGTGCCCTGGCCCACCCTGGTGACCACCCTGGGCTACGG

CGTGCAGTGCTTCGCCCGGTACCCCGACCACATGAAGCAGCACGACTTCT

TCAAGAGCGCCATGCCCGAAGGCTACGTGCAGGAGCGGACCATCTTCTTC

AAGGACGACGGCAACTACAAGACCCGGGCCGAGGTGAAGTTCGAGGGCGA

CACCCTGGTGAACCGGATCGAGCTGAAGGGCATCGACTTCAAGGAGGACG

GCAACATCCTGGGCCACAAGCTGGAGTACAACTACAACAGCCACAACGTG

TACATCACCGCCGACAAGCAGAAGAACGGCATCAAGGCCAACTTCAAGAT

CCGGCACAACATCGAGGACGGCGGCGTGCAGCTGGCCGACCACTACCAGC

AGAACACCCCCATCGGCGACGGCCCCGTGCTGCTGCCCGACAACCACTAC

CTGAGCTACCAGAGCGCCCTGTTCAAGGACCCCAACGAGAAGCGGGACCA

CATGGTGCTGCTGGAGTTCCTGACCGCCGCCGGCATCACCGAGGGCATGA

ACGAGCTCTATAAG

Bold Italics Double Underline: PDGF Transmembrane Domain (Platelet-Derived Growth Factor)

(SEQ ID NO: 9)
GCCGTGGGCCAGGACACCCAGGAGGTGATCGTGGTGCCCCACAGCCTGCC
CTTCAAGGTGGTGGTAATCAGCGCCATCCTGGCACTGGTGGTGCTGACCA
TCATCAGCCTGATCATCCTGATTATGCTGTGGCAGAAGAAGCCCA

---

What is claimed is:

1. A method of selecting an antibody that binds to a protein of interest, the method comprising the steps of:
    a) providing a composition comprising a mammalian cell expressing a protein of interest on the cell surface, wherein the protein of interest comprises at least one unique protease cleavage site, wherein the at least one unique protease cleavage site is a Tobacco Etch Virus nuclear inclusion endopeptidase (TEVprotease) cleavage site;
    b) exposing the mammalian cell to a library of phage-antibody constructs;
    c) binding one or more phage-antibody constructs from the library to the protein of interest to form one or more antigen-antibody complexes, wherein the antigen is the protein of interest;
    d) releasing the one or more antigen-antibody complexes from the cell by cleaving the protease cleavage site with a protease, wherein the protease is a Tobacco Etch Virus nuclear inclusion endopeptidase (TEVprotease);
    e) propagating the released antigen-antibody complexes and identifying the antibody that binds to the protein of interest; thereby selecting the antibody.

2. The method of claim 1, wherein steps (b) through (e) are repeated.

3. The method of claim 2, wherein steps (b) through (e) are repeated from about 2 to about 10 times.

4. The method of claim 1, wherein unbound phage are removed prior to the repeating of steps (b) through (e).

5. The method of claim 1, wherein the protease cleavage site is heterologous to the protein of interest.

6. The method of claim 1, further comprising the step of using the selected antibody to isolate the protein of interest.

7. The method of claim 1, wherein the protein of interest comprises a transmembrane domain.

8. The method of claim 1, wherein the protein of interest comprises at least two transmembrane domains.

9. The method of claim 1, wherein the protein of interest comprises at least two protease cleavage sites, wherein the at least two protease cleavage sites are Tobacco Etch Virus nuclear inclusion endopeptidase (TEVprotease) cleavage sites.

* * * * *

SEQUENCE LISTING

<160> NUMBER OF SEQ ID NOS: 64

<210> SEQ ID NO 1
<211> LENGTH: 6513
<212> TYPE: DNA
<213> ORGANISM: Artificial Sequence
<220> FEATURE:
<223> OTHER INFORMATION: POI Construct Vector

<400> SEQUENCE: 1

| | | | | | |
|---|---|---|---|---|---|
| gacggatcgg | gagatctccc | gatccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgagat | ctctgcagcc | 180 |
| ccgataaaat | aaaagatttt | atttagtctc | cagaaaaagg | ggggaatgaa | agaccccacc | 240 |
| tgtaggtttg | gcaagctagc | tgcagtaacg | ccattttgca | aggcatggaa | aataccaaa | 300 |
| ccaagaatag | agaagttcag | atcaagggcg | ggtacatgaa | aatagctaac | gttgggccaa | 360 |
| acaggatatc | tgcggtgagc | agtttcggcc | ccggcccggg | gccaagaaca | gatggtcacc | 420 |
| gcagtttcgg | ccccggcccg | aggccaagaa | cagatggtcc | ccagatatgg | cccaaccctc | 480 |
| agcagtttct | taagacccat | cagatgtttc | caggctcccc | caaggacctg | aaatgaccct | 540 |
| gcgccttatt | tgaattaacc | aatcagcctg | cttctcgctt | ctgttcgcgc | gcttctgctt | 600 |
| cccgagctct | ataaaagagc | tcacaacccc | tcactcggcg | cgccagtcct | ccgacagact | 660 |
| gagtcgcccg | ggaatacgac | tcactatagg | gagacccaag | ctggctagtt | atcgattagt | 720 |
| gcggccgcca | ccatggagac | agacacactc | ctgctatggg | tactgctgct | ctgggttcca | 780 |
| ggttccactg | gtgactacaa | ggatgacgac | gataagggg | ccagctcggc | ccaggcggtg | 840 |
| cctccatatg | cgtcggagaa | ccagacctgc | agggaccagg | aaaaggaata | ctatgagccc | 900 |
| cagcaccgca | tctgctgctc | ccgctgcccg | ccaggcacct | atgtctcagc | taatgtagc | 960 |
| cgcatccggg | acacagtttg | tgccacatgt | gccgagaatt | cctacaacga | gcactggaac | 1020 |
| tacctgacca | tctgccagct | gtgccgcccc | tgtgacccag | tgatgggcct | cgaggagatt | 1080 |
| gccccctgca | caagcaaacg | gaagacccag | tgccgctgcc | agccgggaat | gttctgtgct | 1140 |
| gcctgggccc | tcgagtgtac | acactgcgag | ctactttctg | actgcccgcc | tggcactgaa | 1200 |
| gccgagctca | agatgaagt | tgggaagggt | aacaaccact | gcgtcccctg | caaggccggg | 1260 |
| cacttccaga | ataccctcctc | ccccagcgcc | cgctgccagc | cccacaccag | gtgtgagaac | 1320 |
| caaggtctgg | tggaggcagc | tccaggcact | gcccagtccg | acacaacctg | caaaaatcca | 1380 |
| ttagagccac | tgcccccaga | gatgtcagga | accatgctga | tgtcggccac | cggggccgga | 1440 |
| tccactagtg | ggggctccgg | ctccgaaaat | ctctacttcc | agagtggcag | cggaggctcc | 1500 |
| gtgagcaaag | gcgaagagct | gttcaccggc | gtggtgccca | tcctggtgga | gctggacggc | 1560 |
| gacgtgaacg | gccacaagtt | cagcgtgagc | ggcgagggcg | agggcgacgc | cacctacggc | 1620 |
| aagctgaccc | tgaagctgct | gtgcaccacc | ggcaagctgc | ccgtgccctg | gcccaccctg | 1680 |
| gtgaccaccc | tgggctacgg | cgtgcagtgc | ttcgcccggt | accccgacca | catgaagcag | 1740 |

```
cacgacttct tcaagagcgc catgcccgaa ggctacgtgc aggagcggac catcttcttc    1800
aaggacgacg gcaactacaa gacccgggcc gaggtgaagt tcgagggcga caccctggtg    1860
aaccggatcg agctgaaggg catcgacttc aaggaggacg gcaacatcct gggccacaag    1920
ctggagtaca actacaacag ccacaacgtg tacatcaccg ccgacaagca gaagaacggc    1980
atcaaggcca acttcaagat ccggcacaac atcgaggacg gcggcgtgca gctggccgac    2040
cactaccagc agaacacccc catcggcgac ggccccgtgc tgctgcccga caaccactac    2100
ctgagctacc agagcgccct gttcaaggac cccaacgaga gcgggaccca catggtgctg    2160
ctggagttcc tgaccgccgc cggcatcacc gagggcatga cgagctcta taagagatcc    2220 ggcggaagcg gtggcggtgg cagcgccgtg ggccaggaca cccaggaggt gatcgtggtg    2280
ccccacagcc tgcccttcaa ggtggtggta atcagcgcca tcctggcact ggtggtgctg    2340
accatcatca gcctgatcat cctgattatg ctgtggcaga agaagcccag gtgagaattc    2400
tgcagatatt cagcacagtg ggggccgctc gagtctagag ggcccgttta aacccgctga    2460
tcagcctcga ctgtgccttc tagttgccag ccatctgttg tttgcccctc ccccgtgcct    2520
tccttgaccc tggaaggtgc cactcccact gtcctttcct aataaaatga ggaaattgca    2580
tcgcattgtc tgagtaggtg tcattctatt ctggggggtg gggtggggca ggacagcaag    2640
ggggaggatt gggaagacaa tagcaggcat gctggggatg cggtgggctc tatggcttct    2700
gaggcggaaa gaaccagctg gggctctagg gggtatcccc acgcgccctg tagcggcgca    2760
ttaagcgcgg cgggtgtggt ggttacgcgc agcgtgaccg ctacacttgc cagcgcccta    2820
gcgcccgctc ctttcgcttt cttcccttcc tttctcgcca cgttcgccgg ctttccccgt    2880
caagctctaa atcgggggct ccctttaggg ttccgattta gtgctttacg gcacctcgac    2940
cccaaaaaac ttgattaggg tgatggttca cgtacctaga agttcctatt ccgaagttcc    3000
tattctctag aaagtatagg aacttccttg gccaaaaagc ctgaactcac gcgacgtct    3060 gtcgagaagt ttctgatcga aaagttcgac agcgtctccg acctgatgca gctctcggag    3120
ggcgaagaat ctcgtgcttt cagcttcgat gtaggagggc gtggatatgt cctgcgggta    3180
aatagctgcg ccgatggttt ctacaaagat cgttatgttt atcggcactt tgcatcggcc    3240
gcgctcccga ttccggaagt gcttgacatt ggggaattca gcgagagcct gacctattgc    3300
atctcccgcc gtgcacaggg tgtcacgttg caagacctgc ctgaaaccga actgcccgct    3360
gttctgcagc cggtcgcgga ggccatggat gcgatcgctg cggccgatct tagccagacg    3420
agcgggttcg gcccattcgg accgcaagga atcggtcaat acactacatg gcgtgatttc    3480
atatgcgcga ttgctgatcc ccatgtgtat cactggcaaa ctgtgatgga cgacaccgtc    3540
agtgcgtccg tcgcgcaggc tctcgatgag ctgatgcttt gggccgagga ctgccccgaa    3600
gtccggcacc tcgtgcacgc ggatttcggc tccaacaatg tcctgacgga caatggccgc    3660
ataacagcgg tcattgactg gagcgaggcg atgttcgggg attcccaata cgaggtcgcc    3720
aacatcttct tctggaggcc gtggttggct tgtatggagc agcagacgcg ctacttcgag    3780
cggaggcatc cggagcttgc aggatcgccg cggctccggg cgtatatgct ccgcattggt    3840
cttgaccaac tctatcagag cttggttgac ggcaatttcg atgatgcagc ttgggcgcag    3900
ggtcgatgcg acgcaatcgt ccgatccgga gccgggactg tcgggcgtac acaaatcgcc    3960
cgcagaagcg cggccgtctg gaccgatggc tgtgtagaag tactcgccga tagtggaaac    4020
cgacgcccca gcactcgtcc gagggcaaag gaatagcacg tactacgaga tttcgattcc    4080
```

```
accgccgcct tctatgaaag gttgggcttc ggaatcgttt tccgggacgc cggctggatg   4140
atcctccagc gcggggatct catgctggag ttcttcgccc accccaactt gtttattgca   4200
gcttataatg gttacaaata aagcaatagc atcacaaatt tcacaaataa agcatttttt   4260
tcactgcatt ctagttgtgg tttgtccaaa ctcatcaatg tatcttatca tgtctgtata   4320
ccgtcgacct ctagctagag cttggcgtaa tcatggtcat agctgtttcc tgtgtgaaat   4380
tgttatccgc tcacaattcc acacaacata cgagccggaa gcataaagtg taaagcctgg   4440
ggtgcctaat gagtgagcta actcacatta attgcgttgc gctcactgcc cgctttccag   4500
tcgggaaacc tgtcgtgcca gctgcattaa tgaatcggcc aacgcgcggg gagaggcggt   4560
ttgcgtattg ggcgctcttc cgcttcctcg ctcactgact cgctgcgctc ggtcgttcgg   4620
ctgcggcgag cggtatcagc tcactcaaag gcggtaatac ggttatccac agaatcaggg   4680
gataacgcag gaaagaacat gtgagcaaaa ggccagcaaa aggccaggaa ccgtaaaaag   4740
gccgcgttgc tggcgttttt ccataggctc cgcccccctg acgagcatca caaaaatcga   4800
cgctcaagtc agaggtggcg aaacccgaca ggactataaa gataccaggc gtttccccct   4860
ggaagctccc tcgtgcgctc tcctgttccg accctgccgc ttaccggata cctgtccgcc   4920
tttctccctt cgggaagcgt ggcgctttct catagctcac gctgtaggta tctcagttcg   4980
gtgtaggtcg ttcgctccaa gctgggctgt gtgcacgaac cccccgttca gcccgaccgc   5040
tgcgccttat ccggtaacta tcgtcttgag tccaacccgg taagacacga cttatcgcca   5100
ctggcagcag ccactggtaa caggattagc agagcgaggt atgtaggcgg tgctacagag   5160
ttcttgaagt ggtggcctaa ctacggctac actagaagga cagtatttgg tatctgcgct   5220
ctgctgaagc cagttacctt cggaaaaaga gttggtagct cttgatccgg caaacaaacc   5280
accgctggta gcggtggttt ttttgtttgc aagcagcaga ttacgcgcag aaaaaaagga   5340
tctcaagaag atcctttgat cttttctacg gggtctgacg ctcagtggaa cgaaaactca   5400
cgttaaggga ttttggtcat gagattatca aaaaggatct tcacctagat ccttttaaat   5460
taaaaatgaa gttttaaatc aatctaaagt atatatgagt aaacttggtc tgacagttac   5520
caatgcttaa tcagtgaggc acctatctca gcgatctgtc tatttcgttc atccatagtt   5580
gcctgactcc ccgtcgtgta gataactacg atacgggagg gcttaccatc tggccccagt   5640
gctgcaatga taccgcgaga cccacgctca ccggctccag atttatcagc aataaaccag   5700
ccagccggaa gggccgagcg cagaagtggt cctgcaactt tatccgcctc catccagtct   5760
attaattgtt gccgggaagc tagagtaagt agttcgccag ttaatagttt gcgcaacgtt   5820
gttgccattg ctacaggcat cgtggtgtca cgctcgtcgt ttggtatggc ttcattcagc   5880
tccggttccc aacgatcaag gcgagttaca tgatccccca tgttgtgcaa aaaagcggtt   5940
agctccttcg gtcctccgat cgttgtcaga agtaagttgg ccgcagtgtt atcactcatg   6000
gttatggcag cactgcataa ttctcttact gtcatgccat ccgtaagatg cttttctgtg   6060
actggtgagt actcaaccaa gtcattctga gaatagtgta tgcggcgacc gagttgctct   6120
tgcccggcgt caatacggga taataccgcg ccacatagca gaactttaaa agtgctcatc   6180
attggaaaac gttcttcggg gcgaaaactc tcaaggatct taccgctgtt gagatccagt   6240
tcgatgtaac ccactcgtgc acccaactga tcttcagcat cttttacttt caccagcgtt   6300
tctgggtgag caaaaacagg aaggcaaaat gccgcaaaaa agggaataag ggcgacacgg   6360
aaatgttgaa tactcatact cttcctttt caatattatt gaagcattta tcagggttat   6420
tgtctcatga gcggatacat atttgaatgt atttagaaaa ataaacaaat aggggttccg   6480
```
cgcacatttc cccgaaaagt gccacctgac gtc                6513

<210> SEQ ID NO 2
<211> LENGTH: 60
<212> TYPE: DNA
<213> ORGANISM: Artificial Sequence
<220> FEATURE:
<223> OTHER INFORMATION: IgKappa signal peptide

<400> SEQUENCE: 2
atggagacag acacactcct gctatgggta ctgctgctct gggttccagg ttccactggt    60

<210> SEQ ID NO 3
<211> LENGTH: 24
<212> TYPE: DNA
<213> ORGANISM: Artificial Sequence
<220> FEATURE:
<223> OTHER INFORMATION: FLAG tag

<400> SEQUENCE: 3
gactacaagg atgacgacga taag                                           24

<210> SEQ ID NO 4
<211> LENGTH: 585
<212> TYPE: DNA
<213> ORGANISM: Artificial Sequence
<220> FEATURE:
<223> OTHER INFORMATION: LTBR antigen

<400> SEQUENCE: 4
gcggtgcctc catatgcgtc ggagaaccag acctgcaggg accaggaaaa ggaatactat    60
gagccccagc accgcatctg ctgctcccgc tgcccgccag gcacctatgt ctcagctaaa   120
tgtagccgca tccgggacac agtttgtgcc acatgtgccg agaattccta caacgagcac   180
tggaactacc tgaccatctg ccagctgtgc cgccccctgt acccagtgat gggcctcgag   240
gagattgccc cctgcacaag caaacggaag acccagtgcc gctgccagcc gggaatgttc   300
tgtgctgcct gggcccctcga gtgtacacac tgcgagctac tttctgactg cccgcctggc   360
actgaagccg agctcaaaga tgaagttggg aagggtaaca accactgcgt cccctgcaag   420
gccgggcact ccagaatac ctcctcccc agcgcccgct gccagccca caccaggtgt    480 gagaaccaag gtctggtgga ggcagctcca ggcactgccc agtccgacac aacctgcaaa   540
aatccattag agccactgcc cccagagatg tcaggaacca tgctg                  585

<210> SEQ ID NO 5
<211> LENGTH: 13
<212> TYPE: DNA
<213> ORGANISM: Artificial Sequence
<220> FEATURE:
<223> OTHER INFORMATION: Cloning site 1 (antigen)

<400> SEQUENCE: 5
ggccagctcg gcc                                                      13

<210> SEQ ID NO 6
<211> LENGTH: 13
<212> TYPE: DNA
<213> ORGANISM: Artificial Sequence
<220> FEATURE:
<223> OTHER INFORMATION: Cloning site 2 (antigen)

<400> SEQUENCE: 6

```
ggccaccggg gcc                                                      13

<210> SEQ ID NO 7
<211> LENGTH: 21
<212> TYPE: DNA
<213> ORGANISM: Artificial Sequence
<220> FEATURE:
<223> OTHER INFORMATION: Tev Protease cleavage site

<400> SEQUENCE: 7
gaaaatctct acttccagag t                                             21

<210> SEQ ID NO 8
<211> LENGTH: 714
<212> TYPE: DNA
<213> ORGANISM: Artificial Sequence
<220> FEATURE:
<223> OTHER INFORMATION: YPET vector

<400> SEQUENCE: 8
gtgagcaaag gcgaagagct gttcaccggc gtggtgccca tcctggtgga gctggacggc    60
gacgtgaacg gccacaagtt cagcgtgagc ggcgagggcg agggcgacgc cacctacggc   120
aagctgaccc tgaagctgct gtgcaccacc ggcaagctgc ccgtgccctg cccacccctg   180
gtgaccaccc tgggctacgg cgtgcagtgc ttcgcccggt accccgacca catgaagcag   240
cacgacttct tcaagagcgc catgcccgaa ggctacgtgc aggagcggac catcttcttc   300
aaggacgacg gcaactacaa gacccgggcc gaggtgaagt tcgagggcga caccctggtg   360
aaccggatcg agctgaaggg catcgacttc aaggaggacg gcaacatcct gggccacaag   420
ctggagtaca actacaacag ccacaacgtg tacatcaccg ccgacaagca gaagaacggc   480
atcaaggcca acttcaagat ccggcacaac atcgaggacg gcgcgtgca gctggccgac   540 cactaccagc agaacacccc catcggcgac ggccccgtgc tgctgcccga caaccactac   600
ctgagctacc agagcgccct gttcaaggac cccaacgaga gcggaccga catggtgctg   660 ctggagttcc tgaccgccgc cggcatcacc gagggcatga cgagctcta taag          714

<210> SEQ ID NO 9
<211> LENGTH: 145
<212> TYPE: DNA
<213> ORGANISM: Artificial Sequence
<220> FEATURE:
<223> OTHER INFORMATION: PDGF transmembrane domain

<400> SEQUENCE: 9
gccgtgggcc aggacaccca ggaggtgatc gtggtgcccc acagcctgcc cttcaaggtg    60
gtggtaatca gcgccatcct ggcactggtg gtgctgacca tcatcagcct gatcatcctg   120
attatgctgt ggcagaagaa gccca                                         145

<210> SEQ ID NO 10
<211> LENGTH: 5
<212> TYPE: PRT
<213> ORGANISM: Artificial Sequence
<220> FEATURE:
<223> OTHER INFORMATION: Enteropeptidase cleavage site

<400> SEQUENCE: 10

Asp Asp Asp Asp Lys
1               5

<210> SEQ ID NO 11
```

```
<211> LENGTH: 6
<212> TYPE: PRT
<213> ORGANISM: Artificial Sequence
<220> FEATURE:
<223> OTHER INFORMATION: Thrombin cleavage site/Factor Xa cleavage site

<400> SEQUENCE: 11

Leu Val Pro Arg Gly Ser
1               5

<210> SEQ ID NO 12
<211> LENGTH: 7
<212> TYPE: PRT
<213> ORGANISM: Artificial Sequence
<220> FEATURE:
<223> OTHER INFORMATION: TEV Protease cleavage site

<400> SEQUENCE: 12

Glu Asn Leu Tyr Phe Gln Gly
1               5

<210> SEQ ID NO 13
<211> LENGTH: 7
<212> TYPE: PRT
<213> ORGANISM: Artificial Sequence
<220> FEATURE:
<223> OTHER INFORMATION: TEV Protease cleavage site

<400> SEQUENCE: 13

Glu Asn Leu Tyr Phe Gln Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Rhinovirus 3C Protease cleavage site

<400> SEQUENCE: 14

Leu Glu Val Leu Phe Gln Gly Pro
1               5

<210> SEQ ID NO 15
<211> LENGTH: 7
<212> TYPE: PRT
<213> ORGANISM: Artificial Sequence
<220> FEATURE:
<223> OTHER INFORMATION: TEV protease cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 15

Glu Xaa Leu Tyr Xaa Gln Xaa
1               5

<210> SEQ ID NO 16
<211> LENGTH: 12
<212> TYPE: PRT
```

```
<213> ORGANISM: Artificial Sequence
<220> FEATURE:
<223> OTHER INFORMATION: Consensus sequence for catalytically active
      ADAM proteins
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 16

His Glu Xaa Gly His Asn Leu Gly Xaa Xaa His Asp
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Catalytic site consensus sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

His Glu Xaa Xaa His
1               5

<210> SEQ ID NO 18
<211> LENGTH: 7
<212> TYPE: PRT
<213> ORGANISM: Artificial Sequence
<220> FEATURE:
<223> OTHER INFORMATION: CDR sequence of anti-GFP clone (A5/L3)

<400> SEQUENCE: 18

Tyr Val Ser Tyr Tyr Leu Phe
1               5

<210> SEQ ID NO 19
<211> LENGTH: 6
<212> TYPE: PRT
<213> ORGANISM: Artificial Sequence
<220> FEATURE:
<223> OTHER INFORMATION: CDR sequence of anti-GFP clone (A5/H1)

<400> SEQUENCE: 19

Ile Ser Tyr Ser Tyr Met
1               5

<210> SEQ ID NO 20
<211> LENGTH: 10
<212> TYPE: PRT
<213> ORGANISM: Artificial Sequence
<220> FEATURE:
<223> OTHER INFORMATION: CDR sequence of anti-GFP clone (A5/H2)

<400> SEQUENCE: 20

Ser Ile Tyr Pro Ser Tyr Ser Tyr Thr Ser
1               5                   10

<210> SEQ ID NO 21
<211> LENGTH: 4
<212> TYPE: PRT
<213> ORGANISM: Artificial Sequence
```

```
<220> FEATURE:
<223> OTHER INFORMATION: CDR sequence of anti-GFP clone (A5/H3)

<400> SEQUENCE: 21

Gly Ser Ala Leu
1

<210> SEQ ID NO 22
<211> LENGTH: 5
<212> TYPE: PRT
<213> ORGANISM: Artificial Sequence
<220> FEATURE:
<223> OTHER INFORMATION: CDR sequence of anti-GFP clone (A7/L3)

<400> SEQUENCE: 22

Ser Trp Gly Leu Ile
1               5

<210> SEQ ID NO 23
<211> LENGTH: 6
<212> TYPE: PRT
<213> ORGANISM: Artificial Sequence
<220> FEATURE:
<223> OTHER INFORMATION: CDR sequence of anti-GFP clone (A7/H1)

<400> SEQUENCE: 23

Ile Ser Tyr Tyr Ser Ile
1               5

<210> SEQ ID NO 24
<211> LENGTH: 10
<212> TYPE: PRT
<213> ORGANISM: Artificial Sequence
<220> FEATURE:
<223> OTHER INFORMATION: CDR sequence of anti-GFP clone (A7/H2)

<400> SEQUENCE: 24

Ser Ile Tyr Pro Tyr Tyr Ser Ser Thr Ser
1               5                   10

<210> SEQ ID NO 25
<211> LENGTH: 9
<212> TYPE: PRT
<213> ORGANISM: Artificial Sequence
<220> FEATURE:
<223> OTHER INFORMATION: CDR sequence of anti-GFP clone (A7/H3)

<400> SEQUENCE: 25

Ala Gly Trp Val Ala Ser Ser Gly Met
1               5

<210> SEQ ID NO 26
<211> LENGTH: 8
<212> TYPE: PRT
<213> ORGANISM: Artificial Sequence
<220> FEATURE:
<223> OTHER INFORMATION: CDR sequence of anti-GFP clone (G3/L3)

<400> SEQUENCE: 26

Ser Ser Ser Gly Ala Ser Pro Ile
1               5

<210> SEQ ID NO 27
<211> LENGTH: 6
<212> TYPE: PRT
<213> ORGANISM: Artificial Sequence
<220> FEATURE:
```

<223> OTHER INFORMATION: CDR sequence of anti-GFP clone (G3/H1)

<400> SEQUENCE: 27

Leu Ser Ser Ser Tyr Ile
1               5

<210> SEQ ID NO 28
<211> LENGTH: 10
<212> TYPE: PRT
<213> ORGANISM: Artificial Sequence
<220> FEATURE:
<223> OTHER INFORMATION: CDR sequence of anti-GFP clone (G3/H2)

<400> SEQUENCE: 28

Ser Ile Tyr Pro Tyr Ser Ser Tyr Thr Tyr
1               5                   10

<210> SEQ ID NO 29
<211> LENGTH: 18
<212> TYPE: PRT
<213> ORGANISM: Artificial Sequence
<220> FEATURE:
<223> OTHER INFORMATION: CDR sequence of anti-GFP clone (G3/H3)

<400> SEQUENCE: 29

Val Pro Tyr Tyr His Tyr Tyr Ser Tyr Pro Gly Trp Val Pro Gly Tyr
1               5                   10                  15

Gly Met

<210> SEQ ID NO 30
<211> LENGTH: 5
<212> TYPE: PRT
<213> ORGANISM: Artificial Sequence
<220> FEATURE:
<223> OTHER INFORMATION: CDR sequence of anti-GFP clone (R3.1/L3)

<400> SEQUENCE: 30

Ala Ser Gly Pro Phe
1               5

<210> SEQ ID NO 31
<211> LENGTH: 5
<212> TYPE: PRT
<213> ORGANISM: Artificial Sequence
<220> FEATURE:
<223> OTHER INFORMATION: CDR sequence of anti-GFP clone (R3.1/H1)

<400> SEQUENCE: 31

Leu Ser Ser Ser Ile
1               5

<210> SEQ ID NO 32
<211> LENGTH: 10
<212> TYPE: PRT
<213> ORGANISM: Artificial Sequence
<220> FEATURE:
<223> OTHER INFORMATION: CDR sequence of anti-GFP clone (R3.1/H2)

<400> SEQUENCE: 32

Ser Ile Tyr Ser Ser Ser Ser Tyr Thr Ser
1               5                   10

<210> SEQ ID NO 33
<211> LENGTH: 5
<212> TYPE: PRT
<213> ORGANISM: Artificial Sequence

```
<220> FEATURE:
<223> OTHER INFORMATION: CDR sequence of anti-GFP clone (R3.1/H3)

<400> SEQUENCE: 33

Tyr Trp Ala Ala Leu
1               5

<210> SEQ ID NO 34
<211> LENGTH: 14
<212> TYPE: PRT
<213> ORGANISM: Artificial Sequence
<220> FEATURE:
<223> OTHER INFORMATION: protease cleavage site and flexible Gly-Ser
      linkers

<400> SEQUENCE: 34

Gly Ser Gly Gly Ser Thr Glu Val Ser Gly Gly Gly Gly Ser
1               5                   10

<210> SEQ ID NO 35
<211> LENGTH: 5
<212> TYPE: PRT
<213> ORGANISM: Artificial Sequence
<220> FEATURE:
<223> OTHER INFORMATION: ANTZR1 R3 Binder Antibody

<400> SEQUENCE: 35

Ser Tyr Gly Leu Phe
1               5

<210> SEQ ID NO 36
<211> LENGTH: 6
<212> TYPE: PRT
<213> ORGANISM: Artificial Sequence
<220> FEATURE:
<223> OTHER INFORMATION: ANTZR1 R3 Binder Antibody

<400> SEQUENCE: 36

Leu Tyr Ser Ser Ser Met
1               5

<210> SEQ ID NO 37
<211> LENGTH: 10
<212> TYPE: PRT
<213> ORGANISM: Artificial Sequence
<220> FEATURE:
<223> OTHER INFORMATION: ANTZR1 R3 Binder Antibody

<400> SEQUENCE: 37

Ser Ile Tyr Ser Tyr Tyr Gly Tyr Thr Tyr
1               5                   10

<210> SEQ ID NO 38
<211> LENGTH: 4
<212> TYPE: PRT
<213> ORGANISM: Artificial Sequence
<220> FEATURE:
<223> OTHER INFORMATION: ANTZR1 R3 Binder Antibody

<400> SEQUENCE: 38

His Trp Ala Leu
1

<210> SEQ ID NO 39
<211> LENGTH: 5
<212> TYPE: PRT
<213> ORGANISM: Artificial Sequence
```

```
<220> FEATURE:
<223> OTHER INFORMATION: ANTZR1 R3 Binder Antibody

<400> SEQUENCE: 39

Ser Tyr Tyr Leu Ile
1               5

<210> SEQ ID NO 40
<211> LENGTH: 6
<212> TYPE: PRT
<213> ORGANISM: Artificial Sequence
<220> FEATURE:
<223> OTHER INFORMATION: ANTZR1 R3 Binder Antibody

<400> SEQUENCE: 40

Leu Ser Ser Tyr Tyr Ile
1               5

<210> SEQ ID NO 41
<211> LENGTH: 10
<212> TYPE: PRT
<213> ORGANISM: Artificial Sequence
<220> FEATURE:
<223> OTHER INFORMATION: ANTZR1 R3 Binder Antibody

<400> SEQUENCE: 41

Tyr Ile Ser Pro Tyr Ser Gly Tyr Thr Ser
1               5                   10

<210> SEQ ID NO 42
<211> LENGTH: 4
<212> TYPE: PRT
<213> ORGANISM: Artificial Sequence
<220> FEATURE:
<223> OTHER INFORMATION: ANTZR1 R3 Binder Antibody

<400> SEQUENCE: 42

Tyr Trp Ala Leu
1

<210> SEQ ID NO 43
<211> LENGTH: 6
<212> TYPE: PRT
<213> ORGANISM: Artificial Sequence
<220> FEATURE:
<223> OTHER INFORMATION: ANTZR1 R3 Binder Antibody

<400> SEQUENCE: 43

Ile Ser Tyr Ser Ser Ile
1               5

<210> SEQ ID NO 44
<211> LENGTH: 10
<212> TYPE: PRT
<213> ORGANISM: Artificial Sequence
<220> FEATURE:
<223> OTHER INFORMATION: ANTZR1 R3 Binder Antibody

<400> SEQUENCE: 44

Ser Ile Tyr Pro Tyr Tyr Gly Tyr Thr Tyr
1               5                   10

<210> SEQ ID NO 45
<211> LENGTH: 4
<212> TYPE: PRT
<213> ORGANISM: Artificial Sequence
<220> FEATURE:
```

<223> OTHER INFORMATION: ANTZR1 R3 Binder Antibody

<400> SEQUENCE: 45

His Trp Gly Met
1

<210> SEQ ID NO 46
<211> LENGTH: 5
<212> TYPE: PRT
<213> ORGANISM: Artificial Sequence
<220> FEATURE:
<223> OTHER INFORMATION: ANTZR1 R3 Binder Antibody

<400> SEQUENCE: 46

Ser Phe Tyr Leu Ile
1               5

<210> SEQ ID NO 47
<211> LENGTH: 6
<212> TYPE: PRT
<213> ORGANISM: Artificial Sequence
<220> FEATURE:
<223> OTHER INFORMATION: ANTZR1 R3 Binder Antibody

<400> SEQUENCE: 47

Leu Tyr Tyr Ser Ser Met
1               5

<210> SEQ ID NO 48
<211> LENGTH: 4
<212> TYPE: PRT
<213> ORGANISM: Artificial Sequence
<220> FEATURE:
<223> OTHER INFORMATION: ANTZR1 R3 Binder Antibody

<400> SEQUENCE: 48

Tyr Trp Ala Phe
1

<210> SEQ ID NO 49
<211> LENGTH: 6
<212> TYPE: PRT
<213> ORGANISM: Artificial Sequence
<220> FEATURE:
<223> OTHER INFORMATION: ANTZR1 R3 Binder Antibody

<400> SEQUENCE: 49

Phe Ser Ser Ser Ser Ile
1               5

<210> SEQ ID NO 50
<211> LENGTH: 4
<212> TYPE: PRT
<213> ORGANISM: Artificial Sequence
<220> FEATURE:
<223> OTHER INFORMATION: ANTZR1 R3 Binder Antibody

<400> SEQUENCE: 50

Ser Trp Gly Met
1

<210> SEQ ID NO 51
<211> LENGTH: 6
<212> TYPE: PRT
<213> ORGANISM: Artificial Sequence
<220> FEATURE:
<223> OTHER INFORMATION: LTBR R3 Binder Antibody

```
<400> SEQUENCE: 51

Ser Ser Tyr Ser Leu Ile
1               5

<210> SEQ ID NO 52
<211> LENGTH: 10
<212> TYPE: PRT
<213> ORGANISM: Artificial Sequence
<220> FEATURE:
<223> OTHER INFORMATION: LTBR R3 Binder Antibody

<400> SEQUENCE: 52

Ser Ile Tyr Pro Ser Tyr Gly Tyr Thr Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: LTBR R3 Binder Antibody

<400> SEQUENCE: 53

Pro Ala Gly Tyr Phe Trp Gly Ser Ser Trp Phe Trp Gly Phe
1               5                   10

<210> SEQ ID NO 54
<211> LENGTH: 8
<212> TYPE: PRT
<213> ORGANISM: Artificial Sequence
<220> FEATURE:
<223> OTHER INFORMATION: LTBR R3 Binder Antibody

<400> SEQUENCE: 54

Ser Trp Gly Val Ala Tyr Pro Ile
1               5

<210> SEQ ID NO 55
<211> LENGTH: 6
<212> TYPE: PRT
<213> ORGANISM: Artificial Sequence
<220> FEATURE:
<223> OTHER INFORMATION: LTBR R3 Binder Antibody

<400> SEQUENCE: 55

Ile Tyr Ser Ser Ser Met
1               5

<210> SEQ ID NO 56
<211> LENGTH: 10
<212> TYPE: PRT
<213> ORGANISM: Artificial Sequence
<220> FEATURE:
<223> OTHER INFORMATION: LTBR R3 Binder Antibody

<400> SEQUENCE: 56

Ser Ile Ser Ser Tyr Ser Ser Tyr Thr Ser
1               5                   10

<210> SEQ ID NO 57
<211> LENGTH: 6
<212> TYPE: PRT
<213> ORGANISM: Artificial Sequence
<220> FEATURE:
<223> OTHER INFORMATION: LTBR R3 Binder Antibody
```

```
<400> SEQUENCE: 57

Ser Phe Tyr Ser Ala Met
1               5

<210> SEQ ID NO 58
<211> LENGTH: 6
<212> TYPE: PRT
<213> ORGANISM: Artificial Sequence
<220> FEATURE:
<223> OTHER INFORMATION: LTBR R3 Binder Antibody

<400> SEQUENCE: 58

Pro Gly Tyr His Leu Ile
1               5

<210> SEQ ID NO 59
<211> LENGTH: 6
<212> TYPE: PRT
<213> ORGANISM: Artificial Sequence
<220> FEATURE:
<223> OTHER INFORMATION: LTBR R3 Binder Antibody

<400> SEQUENCE: 59

Leu Ser Tyr Tyr Ser Met
1               5

<210> SEQ ID NO 60
<211> LENGTH: 10
<212> TYPE: PRT
<213> ORGANISM: Artificial Sequence
<220> FEATURE:
<223> OTHER INFORMATION: LTBR R3 Binder Antibody

<400> SEQUENCE: 60

Ser Ile Tyr Ser Ser Tyr Gly Tyr Thr Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: LTBR R3 Binder Antibody

<400> SEQUENCE: 61

Trp Tyr Gly Phe Tyr Val Gly His Gly Ser Tyr Ala Met
1               5                   10

<210> SEQ ID NO 62
<211> LENGTH: 6
<212> TYPE: PRT
<213> ORGANISM: Artificial Sequence
<220> FEATURE:
<223> OTHER INFORMATION: LTBR R3 Binder Antibody

<400> SEQUENCE: 62

Ile Tyr Ser Tyr Ser Met
1               5

<210> SEQ ID NO 63
<211> LENGTH: 10
<212> TYPE: PRT
<213> ORGANISM: Artificial Sequence
<220> FEATURE:
<223> OTHER INFORMATION: LTBR R3 Binder Antibody

<400> SEQUENCE: 63
```

```
Tyr Ile Tyr Pro Ser Tyr Gly Ser Thr Tyr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: LTBR R3 Binder Antibody

<400> SEQUENCE: 64

Trp Tyr Trp Trp Tyr Gly Gly Ser Gly Ser Gly Tyr Ala Met
1               5                   10
```